(12) United States Patent
Dellinger

(10) Patent No.: US 8,846,898 B2
(45) Date of Patent: Sep. 30, 2014

(54) PHOSPHINOAMIDITE CARBOXYLATES AND ANALOGS THEREOF IN THE SYNTHESIS OF OLIGONUCLEOTIDE HAVING REDUCED INTERNUCLEOTIDE CHARGE

(75) Inventor: Douglas J. Dellinger, Sunnyvale, CA (US)

(73) Assignee: Lieure Cornu LLC, Boulder, CO (US)

( * ) Notice: Subject to any disclaimer, the term of this patent is extended or adjusted under 35 U.S.C. 154(b) by 649 days.

(21) Appl. No.: 12/464,337

(22) Filed: May 12, 2009

(65) Prior Publication Data

US 2010/0311960 A1 Dec. 9, 2010

Related U.S. Application Data

(62) Division of application No. 11/431,373, filed on May 9, 2006, now Pat. No. 7,745,591, which is a division of application No. 10/721,301, filed on Nov. 24, 2003, now Pat. No. 7,067,641, which is a division of application No. 09/691,824, filed on Oct. 17, 2000, now Pat. No. 6,693,187.

(51) Int. Cl.
| | |
|---|---|
| *C07H 19/04* | (2006.01) |
| *C07C 229/00* | (2006.01) |
| *C07C 53/00* | (2006.01) |
| *C07H 21/02* | (2006.01) |
| *C07H 19/20* | (2006.01) |
| *C07H 21/00* | (2006.01) |
| *C07H 19/10* | (2006.01) |
| *C07H 21/04* | (2006.01) |

(52) U.S. Cl.
CPC ............... *C07H 21/00* (2013.01); *C07H 21/02* (2013.01); *C07H 19/20* (2013.01); *C07H 19/10* (2013.01); *C07H 21/04* (2013.01); *C07B 2200/11* (2013.01)
USPC .......................... 536/26.1; 560/170; 562/512

(58) Field of Classification Search
None
See application file for complete search history.

(56) References Cited

PUBLICATIONS

AN# 1968:486088—Petrovshaya et al., 1968.*
AN 1972:14875, Nifant'ev et al., Zhurnal Obshchei Khimii, 1971, 41(9), 2104-5, abstract.*
Soleilhavoup et al., Inorganic chemistry, vol. 31, No. 8, 1992, pp. 1500-1504.*
AN 1977:5541, Karlstedt et al, Khim. Elementoorg. Soedin, 1976, 172-5, abstract.*
AN 1976:405798, Novikova et al., Zhurnal Obshchei Khimii, 1976, 46(3), 575-8, abstract.*
Supplementary European Search Report for EP 01 98 3160, dated Dec. 11, 2006 (4 pages).
Caruthers, H.H. et al. (1987) Synthesis of Oligonucleotides Using the Phosphramidite Method, in Bioactive Molecules, vol. 3, pp. 3-21, Elsevier, Amsterdam NL.
Dellinger, D.J. et al (2003) Solid-phase Chemical Synthesis of Phosphonoacetate and Thiophosphonoacetate Oligodeoxynucleotides, Journal of the American Chemical Society, 125(4):940-050.
Rudolph, M.J. et al. (1996) Phosphonoacetate Derivatives of Oligodeoxynucleotides, Nucleosides and Nucleotides, 15/11-12:1725-1739.
Karlstedt, N.B. et al. (1976) Dialkoxyphosphines. III. Reaction of Dialkoxyphosphines with Alkali Metal Dialkylamines; Amido Esters of Hypophosphorous Acid; Abstract; STN Database Accesion No. 86:5541; Khim Elementorg. Soedin 172-5; Editos: Danilov, S.N.; publisher: "Nauka," Leningr. otd., Leningrad, USSR; Coden; 33YRAV, 1978.
Marugg, J.E. et al (1986) A New and Versatile Approach to the Preparation of Valuable Deoxynucleoside 3-Phosphite Intermediates, Tetrahedron Lett. 27/20:2271-2274.
Stepanov, I.A. et al. (1979) Synthesis of Phosphorus(III) Compounds Containing an Alpha-carboalkyoxymethyle Group; Abstract; STN Database Accession No. 92:129019, Zhurnal Obshscei Khimi (1979), 49(10), 2389; Coden; ZOKHA4; ISSN:0044-460X, 1979.
Yamada, C.M. et al (2006) Synthesis and Biochemical Evaluation of Phosphonoformate Oligodeoxyribonucleotides, Journal of the American Chemical Society 128(15):5251-5261.
Lambert et al (1989) Synthesis and Antiviral Activity of Phosphonoacetic and Phosphonoformic Act esters. J. Med. Chem.32/2:367-374.

* cited by examiner

*Primary Examiner* — Traviss C McIntosh, III

(57) ABSTRACT

Nucleoside phosphinoamidite carboxylates and analogs are provided that have the structure of formula (III)

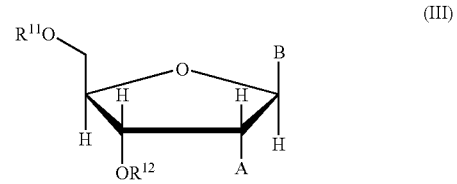

(III)

wherein A is hydrogen, hydroxyl, lower alkoxy, lower alkoxy-substituted lower alkoxy, halogen, SH, $NH_2$, azide or DL wherein D is O, S or NH and L is a heteroatom-protecting group, unsubstituted hydrocarbyl, substituted hydrocarbyl, heteroatom-containing hydrocarbyl, or substituted heteroatom-containing hydrocarbyl; B is a nucleobase; and one of $R^{11}$ and $R^{12}$ is a blocking group and the other is (IV) or (VI)

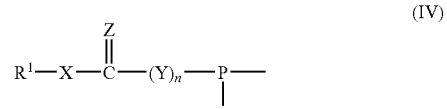

(IV)

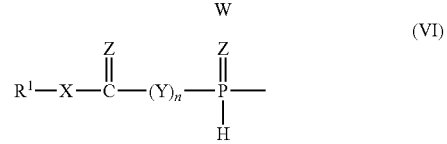

(VI)

in which W, X, Y, Z, $R^1$ and n are as defined herein.

20 Claims, 9 Drawing Sheets

Figure 1: Synthesis Cycle for Phosphonoacetate Polynucleotides

Figure 2: Synthesis Cycle for Phosphonothioacetate Polynucleotides

PHOSPHINOAMIDITE CARBOXYLATES AND ANALOGS THEREOF IN THE SYNTHESIS OF OLIGONUCLEOTIDE HAVING REDUCED INTERNUCLEOTIDE CHARGE

CROSS-REFERENCE TO RELATED APPLICATIONS

This is a divisional application of U.S. Ser. No. 11/431,373, filed May 9, 2006 now U.S. Pat. No. 7,745,591 which is a divisional application of U.S. Ser. No. 10/721,301, filed Nov. 24, 2003, now U.S. Pat. No. 7,067,641, which is a divisional application of U.S. Ser. No. 09/691,824, filed Oct. 17, 2000, now U.S. Pat. No. 6,693,187. The disclosures of the aforementioned applications are incorporated by reference.

TECHNICAL FIELD

This invention relates generally to the fields of nucleic acid chemistry and oligonucleotide synthesis, and more particularly relates to novel phosphinoamidite carboxylates and analogs thereof in the synthesis of oligonucleotides having reduced internucleotide charge and enhanced nuclease resistance, i.e., phosphinocarboxylate oligonucleotides, phosphonocarboxylate oligonucleotides, and analogs thereof.

BACKGROUND

The derivatives of phosphoric acid have been shown to have a wide range of biological utility (Ernsley and Hall (1976) in *The Chemistry of Phosphorus: Chapter 12 Biophosphorus Chemistry* pp. 471-510 Harper and Row: London, England). In turn, molecules that mimic phosphoric acid and its derivatives have been shown to work as biological effectors and are often used as diagnostic and therapeutic agents (Uhlmann and Peyman (1990) *Chem. Rev.* 90: 544). Examples of these derivatives are phosphonocarboxylates (Becker et al. (1977) *Antimicrob. Agents Chemother.Ys:* 919), phosphorothioates (Eckstein (1989) *Trends Biochem. Sci.* 14: 97), phosphorodithioates (Nielsen et al. (1988) *Tetrahedron Lett.* 29: 2911), methylphosphonates (Miller and Ts'o (1988) *Annu. Rep. Med. Chem.* 23: 295). and phosphoramidates (Iyer et al. (1996) *Tetrahedron Lett.* 37: 1543).

Phosphonocarboxylate mimics of phosphoric acid, specifically phosphonoformic acid and phosphonoacetic acid, have been shown to be especially useful as biological effectors and have been used as therapeutic agents (Shipkowitz et al. (1973) *Appl. Microbiol.* 26: 264; Helgestrand et al. (1978) *Science* 201: 819). The syntheses of phosphonoformic acid (Nylen (1924) *Chem Berichte.* 57: 1023) and phosphonoacetic acid (Basinger et al. (1959) *J. Org. Chem.* 24: 434) have relied upon the introduction of the carboxylate group onto the phosphorus moiety through an oxidative transformation such as a Michaelis-Arbuzov reaction (Arbuzov and Dunin (1914) *J. Chem. Soc.* 653; Arbuzov (1964) *Pure Appl. Chem.* 9: 307). The resulting phosphonocarboxylic acid products are in the oxidation state P(V). Once the phosphorus atom is in this pentacoordinate oxidation state the products are typically very stable. However, these stable products are difficult and sometimes impossible to utilize in performing high yielding chemical transformations, chemical couplings, or chemical derivatizations. As a result of the low chemical reactivity of these pentacoordinate phosphorus molecules, many biologically important molecules that exist as phosphoric acid derivatives have not been mimicked with phosphonocarboxylic acid derivatives (Hildebrand (1983), in *The Role of Phosphonates in Living Systems*: Chapters 5 & 6, pp. 97-169, CRC Press Inc: Boca Raton, USA).

Two clear examples of biologically important molecules that exist naturally as phosphoric acid derivatives and have not been mimicked as phosphonocarboxylic acid derivatives are the polynucleotides DNA and RNA. Polynucleotides modified at the phosphodiester internucleotide linkage are of significant interest to the emerging fields of antisense therapeutics, nucleic acid diagnostics, and genomics. Phosphorus-containing chemical compounds and compositions that have been successfully utilized to enable the synthesis of polynucleotides have been frequently reviewed in the scientific literature (Verma et al. (1998) *Annu. Rev. Biochem.* 67:99; Sekine et. al. (1998) *Nucleosides and Nucleotides* 17:2033; Iyer et al (1999) *Curr. Opin. Mol. Ther.* 1:344). The successful chemical synthesis of polynucleotides or modified polynucleotides is a task especially dependent upon the ability to find and employ phosphorus-containing compounds that enable high yield chemical couplings and chemical transformations (Caruthers (1985) *Science* 230:281; Caruthers et al., U.S. Pat. No. 4,415,732, issued Nov. 15, 1983). To enable the chemical synthesis of polynucleotides or modified polynucleotides, the phosphorus compounds used must be able to perform high yield coupling reactions that are general to the four nucleobases and specific for the desired polynucleotide products. High yield coupling efficiencies for the formation of internucleotide bonds are necessary in order to enable the synthesis of biologically relevant lengths of polynucleotides (Koster et al., U.S. Pat. No. 4,725,677 issued Feb. 16, 1988), wherein a "biologically relevant length" is a length that allows the polynucleotide to stably and specifically bind to other polynucleotides by hybridization through base-pairing interactions. Stable binding of polynucleotides to other polynucleotides via hybridization is also affected by temperature, salt concentration, nucleotide sequence, and other factors, as has been extensively discussed in the literature; see, e.g., Sanger (1984) in *Principles of Nucleic Acid Structure*: Chapter 6, pp. 116-158 (Springer-Verlag: New York, USA).

The need for high yield coupling reactions in synthesizing polynucleotides of a biologically relevant length is due to the mathematical relationship between the final yield of the desired polynucleotide product and the efficiency for each individual coupling reaction giving rise to a new internucleotide bond. The final yield of the desired polynucleotide product is a multiplication product of all individual coupling and deprotection steps required in achieving that product. As a result, the yield of the final polynucleotide product decreases exponentially with a linear decrease in the coupling efficiency. That is, the effect of the coupling efficiency on the overall yield of product can be described by the equation $Y = X^N$, where Y is the fractional overall yield, X is the fractional coupling efficiency, and N is the number of couplings. For the synthesis of a typical polynucleotide 20 nucleotides in length with 19 internucleotide linkages, 19 coupling reactions are involved and the overall yield is given by $Y = X^{19}$. The table below illustrates the relationship between the coupling efficiency (X) and overall yield of polynucleotide product (Y).

| | X | | | | | | | | | | |
|---|---|---|---|---|---|---|---|---|---|---|---|
| | 0.10 | 0.20 | 0.30 | 0.40 | 0.50 | 0.60 | 0.70 | 0.80 | 0.90 | 0.95 | 0.99 |
| Y | $1^{-19}$ | $5^{-14}$ | $1^{-10}$ | $3^{-3}$ | $2^{-6}$ | $6^{-5}$ | $1^{-3}$ | $1^{-2}$ | 0.14 | 0.38 | 0.82 |

As clearly illustrated by this example, and as well known by those skilled in the art, the synthesis of a 20-mer polynucleotide is not possible until the coupling efficiency achieved during synthesis approaches 90% or greater. Only at these coupling efficiencies can full-length polynucleotides be reproducibly isolated and purified from the reaction mixtures. As a further example for illustration, at an 80% coupling efficiency, the theoretical maximum amount of full-length product (Y), after 19 couplings, is 1.4%. However, the overall yield shown in the table above is a simplification that considers only the effect of the efficiency for the formation of the internucleotide bond. The actual overall yield of a polynucleotide product is additionally adversely affected by any inefficiency in deprotection reactions used during synthesis, post-synthesis, or from side-reactions leading to undesired products. The ability to isolate a full-length polynucleotide product, 20 nucleotides in length, from a polynucleotide synthesis that achieves an 80% per cycle coupling efficiency is precarious and rarely reproducible, and directly linked to the yield of the individual deprotection reactions following each coupling step. As a direct result of these requirements for high yield reactions, the chemical synthesis of polynucleotides has been accomplished by only very few methods; see Brown (1983) in *Protocols for Oligonucleotides and Analogs*: Chapters 1, pp. 1-17 (Humana Press: Totowa, N.J., USA, Ed. S. Agrawal). Each of the methods that has enabled the chemical synthesis of polynucleotides has in turn been enabled by the development of high yielding coupling reactions at the phosphorus moiety, in concert with the development of high yielding deprotection reactions. The fact that so few methods have enabled polynucleotide synthesis is a direct result of the difficulty of performing a long series of sequential chemical reactions in quantitative or near-quantitative yields.

The chemical synthesis of polynucleotides containing the naturally occurring phosphodiester linkage was originally accomplished using nucleotide building blocks known as "diester intermediates." These "diester" building blocks were nucleotide monomers on which the heterocyclic bases and exposed hydroxyl functionality were chemically protected by blocking groups, and the pendant phosphate group activated for transesterification reactions by the formation of a "phosphodiester" (Gilham & Khorana (1958) *J. Amer. Chem Soc.* 80: 6212). The low reactivity of these activated P(V) monomers resulted in low synthetic yields for internucleotide bond formation. The typical yield for the coupling of nucleoside phosphodiester monomers to nucleoside or nucleotide hydroxyl groups is in the range of 20-50%. The low synthetic yields achieved by these chemical coupling reactions limited this method to the synthesis of monomer, dimer, and trimer products. The synthesis of biologically relevant lengths of polynucleotides from these monomer, dimer, and trimer blocks was accomplished by the use of an enzymatic ligation reaction (Khorana (1966) *The Harvey Lectures, ser.* 62, pp. 79-106; Khorana, H. G. (1979) *Science* 203: 614). This enzymatic process was dependent upon these monomer, dimer, and trimer blocks acting as high yielding substrates for enzymatic ligation reactions, and on the enzymatic reactions producing the desired naturally occurring phosphodiester internucleotide bond. The complete chemical synthesis of these polynucleotides could not be demonstrated as a result of the low coupling efficiencies of phosphodiester intermediates for the formation of internucleotide bonds.

The complete chemical synthesis of polynucleotides containing naturally occurring phosphodiester internucleotide linkages was first made possible by the development of phosphotriester reactive intermediates (Narang et. al. (1980) *Methods in Enzymology* 65:610) and phosphite reactive intermediates (Letsinger & Lunsford (1976) *J. Am. Chem. Soc.* 98:3655; Beaucage & Caruthers (1981) *Tetrahedron Lett.* 22:1859). Phosphotriester reactive intermediates produced coupling efficiencies for the formation of internucleotide bonds in the range of 65-87% depending upon the sequence and condensing agent utilized (Efimov et. al. (1982) *Nucleic Acids Research* 10:6675). In the lower end of this range of coupling efficiencies, the enzymatic ligation of block-coupled products was required to enable the synthesis and isolation of polynucleotides. In the upper end of the range of coupling efficiencies, it was difficult but possible to isolate full-length polynucleotides from the reaction products of a complete chemical synthesis. The subsequent development of phosphite reactive intermediates produced coupling efficiencies for the formation of internucleotide bonds in the range of 90-99%. It was the invention of these phosphite chemical compositions of protected nucleosides, in concert with effective protecting group chemistry, that enabled the routine chemical synthesis of native polynucleotides (Matteucci & Caruthers (1981) *J. Am. Chem. Soc.* 103: 3185).

The chemical synthesis of phosphorus-backbone modified polynucleotides is more difficult than the chemical synthesis of naturally occurring phosphodiester-linked polynucleotides. Modification of the phosphorus backbone, in most cases, precludes the use of high yielding enzymatic ligation methods. The enzymes that are typically used for the formation of internucleotide bonds have substrate fidelity requirements that make it difficult if not impossible to use them to form backbone-modified internucleotide bonds. A few phosphorus backbone modifications, such as phosphorothioates, have been formed using enzymatic incorporation of modified nucleotides or enzymatic ligation reactions, but these modifications tend to be rare and the reactions much less efficient than the formation of native internucleotide bonds (Eckstein (1985) *Annu. Rev. Biochem.* 54:367). Without the ability to overcome low coupling efficiencies using enzymatic ligation of dimer and trimer blocks, the enablement of backbone-modified polynucleotides is even more rigorously tied to the need for high yielding coupling reactions and high yielding deprotection reactions than is the synthesis of phosphodiester-linked polynucleotides.

Nucleotide monomers of phosphonocarboxylates, phosphonoformic acid and phosphonoacetic acid (Heimer et. al., U.S. Pat. No. 4,056,673 issued Nov. 1, 1977; Sekine et. al. (1982) *Bull. Chem. Soc. Jpn.* 55: 239; Griengl et. al. (1988) *J. Med. Chem.* 31: 1831; Lambert et. al. (1989) *J. Med. Chem.* 32: 367) have been prepared using protected nucleosides and the activated transesterification techniques developed for phosphodiester and phosphotriester coupling of internucleotide bonds (Shaller et. al. (1963) *J. Am. Chem. Soc.* 85: 3821; Amarnath et al. (1977) *Chem. Rev.* 77: 183). These modified nucleotide monomers have been shown to be inhibitory to DNA and RNA polymerases and have not proved to be efficient substrates for enzymatic incorporation or ligation. As a result, the enablement of phosphonocarboxylate derivatives of polynucleotides requires the ability to perform complete chemical synthesis, in turn requiring high yielding coupling reactions and high yielding deprotection reactions.

Prior to the current invention, attempts by the present inventor to chemically synthesize phosphonocarboxylate modified polynucleotides were performed using the chemical reactions previously reported for coupling alkyl esters of phosphonoformic acid and phosphonoacetic acid to protected nucleosides. 3'-Phosphonocarboxylate protected nucleotide monomers were prepared and isolated by literature protocols. A series of attempts were then made to produce polynucleotides with phosphonocarboxylate-modified internucleotide linkages by applying one of the many standard phosphotriester condensing agents on solid-phase (Stawinski et. al. (1977) *Nucleic Acids Res.* 4: 353; Reese et. al. (1978) *Tetrahedron Lett.* 19: 2727). All of these attempts to form internucleotide bonds using activated transesterification methods on the P(V) phosphonocarboxylates of protected nucleosides, gave coupling efficiencies too poor to enable the synthesis of polynucleotides. Although the coupling efficiencies were extremely low (<10%), solution-phase coupling of these modified nucleotides to 3'-protected nucleosides allowed for isolation of a small amount of thymidine-thymidylate protected dimers with phosphonoformate and phosphonoacetate internucleotide bonds. Attempts to deprotect the ethyl or methyl esters of the carboxylic acid phosphonate dimers, by the hydrolysis methods previously published for nucleotide monophosphonocarboxylates, led to cleavage of the internucleotide bond. Using base-catalyzed, nucleophilic hydrolysis conditions to deprotect the carboxylic acid methyl or ethyl esters of phosphonoformate and phosphonoacetate thymidine-thymidylate dimers, resulted in significant cleavage of the phosphorus-carbon bond (40%-100%). Analysis of the products from these nucleophilic hydrolysis reactions demonstrated cleavage of the phosphorus-carbon bond that in turn resulted in both cleavage of the internucleotide bond, and conversion of the modified internucleotide bond to a phosphodiester bond. A subsequent literature study confirmed these observations and revealed that the phosphorus-carbon bond of acylphosphonates was susceptible to cleavage under the conditions of carboxylate ester hydrolysis. The facile loss of similar phosphorus-carbon bonds had been previously observed under the conditions of nucleophilic hydrolysis and a mechanism proposed (Sekine et al. (1980) *J. Org. Chem.* 45: 4162; Narayanan et. al (1979) *J. Am. Chem. Soc.* 101: 109; Kluger et. al. (1978) *J. Am. Chem. Soc.* 100: 7382). The nucleophilic attack of hydroxide or other nucleophile on the carbonyl of phosphonocarboxylates result in the formation of a tetrahedral intermediate containing a localized negative charge on the oxygen of the carbonyl. Further rearrangement of this intermediate results in reaction products that favor cleavage of the phosphorus-carbon bond rather than the desired substitution by hydroxide. Once again, there is a high yield requirement for these deprotection reactions in order to enable the synthesis and isolation of phosphonocarboxylic acid modified polynucleotides. Non-quantitative deprotection reactions at the internucleotide linkage or rearrangement products that lead to undesired side-products has an exponentially negative effect on the yield of full-length polynucleotide product. Moderate to low yields for the removal of protecting groups, or cleavage of the phosphorus-carbon bond during deprotection of the carboxylic acid thus directly prevents the enablement of these modified polynucleotides. Although one reference describes synthesis of phosphonocarboxylic acid modified polynucleotides as feasible (Cook et al., International Patent Publication No. WO 93/10140), in fact the methods described, or similar activated transesterification methods, do not enable the synthesis of phosphonocarboxylic acid modified polynucleotides.

Rudolph et. al (1996) *Nucleosides and Nucleotides* 15:1725 describe the solution-phase synthesis of thymidine-thymidylate dimers containing methyl phosphonoacetate internucleotide bonds using an activated transesterification method with 1-(2-mesitylene-sulfonyl)-3-nitro-1,2,4-triazole (MSNT) and a pentavalent phosphonoacetate derivative. In order to incorporate this dimer modification into longer polymers the authors derivatized the dimer with a standard phosphoramidite reagent (Atkinson et al. (1984) *Oligonucleotide Synthesis: A Practical Approach*, Gait, Ed., IRL Press, Oxford, pp 41-45) and used the high yielding formation of native internucleotide phosphodiester bonds to assemble longer polymers, containing only the nucleobase thymidine, with the assumption that every other linkage in the resulting reaction mixture would be a phosphonoacetate. The publication additionally reported that the phosphonoacetate group is labile to ammonium hydroxide, hydrazine, ethylenediamine, triethylamine/water, and piperidine/water, resulting in the cleavage of the internucleotide bond. The conditions reported to give complete cleavage of the internucleotide bond are the same conditions that are reported in WO 93/10140. As in the aforementioned PCT publication, Rudolph et al. clearly demonstrated that the activated transesterification coupling of protected nucleoside, P(V) alkyl phosphonocarboxylates and subsequent hydrolytic cleavage of alkyl ester protected carboxylic acid groups does not enable the synthesis of phosphonocarboxylic acid modified polynucleotides.

There are few reported phosphorus chemical compositions in the oxidation state P(III) having protected carboxylic acid functional groups. Reports of phosphinylacetic acid derivatives are uncommon, and have been exclusively studied for their unique physical (Matrosov et. al. (1972) *Zh. Obshch. Khim.* 42: 1695) and chemical (Podlahova, J. (1978) *Collection Czechoslov. Chem. Commun.* 43: 57) properties rather than their use as chemical synthons. Also see Novikova et. al. (1976) *Zh. Obshch. Khim.* 46: 575; Novikova et. al. (1976) *Zh. Obshch. Khim.* 46: 2213; and Stepanov et. al. (1979) *Zh. Obshch. Khim.* 49: 2389)

The low chemical reactivity of pentacoordinate phosphonocarboxylate molecules has prevented the incorporation of internucleotide phosphonocarboxylate moieties into many biologically important molecules. Preparation of oligonucleotides containing internucleotide phosphonocarboxylate moieties would require chemical compositions of phosphorus that perform high yielding chemical couplings and chemical transformations. More particularly, chemical synthesis of phosphonocarboxylate oligonucleotides and polynucleotides (DNA and RNA) would require both high yielding coupling reactions at the phosphorus moiety and high yielding deprotection reactions at the carboxylate moiety, with the phosphorus-carboxylate moiety left intact.

SUMMARY OF THE INVENTION

Accordingly, it is a primary object of the invention to provide compounds and methods for synthesizing oligonucleotides containing internucleotide phosphinocarboxylate and phosphonocarboxylate linkages and analogs thereof.

It is another object of the invention to provide such compounds and methods wherein chemical synthesis of the oligonucleotides proceeds via high yielding coupling reactions at the phosphorus moiety as well as high yielding reactions at the carboxylate moiety, with the phosphorus-carboxylate moiety left intact.

It is another object of the invention to provide phosphinocarboxylate oligonucleotides, phosphonocarboxylate oligonucleotides, and analogs thereof synthesized using the aforementioned compounds and methods.

It is an additional object of the invention to provide methods for using the novel phosphinocarboxylate and phosphonocarboxylate oligonucleotides.

Additional objects, advantages and novel features of the invention will be set forth in part in the description which follows, and in part will become apparent to those skilled in the art upon examination of the following, or may be learned by practice of the invention.

In one embodiment of the invention, then, phosphinoamidite carboxylates and analogs thereof are provided having the structure of formula (I)

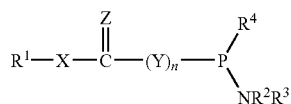

wherein: $R^1$ is hydrogen, a protecting group removable by an elimination reaction, hydrocarbyl, substituted hydrocarbyl, heteroatom-containing hydrocarbyl, or substituted heteroatom-containing hydrocarbyl; $R^2$ and $R^3$ are independently selected from the group consisting of hydrocarbyl, substituted hydrocarbyl, heteroatom-containing hydrocarbyl and substituted heteroatom-containing hydrocarbyl, or $R^2$ and $R^3$ are linked to form a substituted or unsubstituted, five- or six-membered nitrogen-containing heterocycle; $R^4$ is $NR^5R^6$, halogen or DL, wherein $R^5$ and $R^6$ are independently selected from the group consisting of hydrocarbyl, substituted hydrocarbyl, heteroatom-containing hydrocarbyl and substituted heteroatom-containing hydrocarbyl, or $R^5$ and $R^6$ are linked to form a substituted or unsubstituted, five- or six-membered nitrogen-containing heterocycle, D is O, S or NH, and L is a heteroatom-protecting group, unsubstituted hydrocarbyl, substituted hydrocarbyl, heteroatom-containing hydrocarbyl, or substituted heteroatom-containing hydrocarbyl; X is O, S NH or $NR^7$ wherein $R^7$ is hydrocarbyl, substituted hydrocarbyl, heteroatom-containing hydrocarbyl or substituted heteroatom-containing hydrocarbyl; n is zero or 1; Y is —$(Y')_m$—$(CR^8R^9)$— wherein m is zero or 1, Y' is hydrocarbylene, substituted hydrocarbylene, heteroatom-containing hydrocarbylene, or substituted heteroatom-containing hydrocarbylene, wherein $R^8$ and $R^9$ are as defined for $R^1$, with the proviso that when n is 1, m is zero and $R^8$ and $R^9$ are both hydrogen, then $R^1$ is hydrogen or a protecting group removable by an elimination reaction; and Z is O, S, NH or $NR^{10}$ wherein $R^{10}$ is as defined for $R^7$.

Compounds of formula (I) are useful as phosphitylating agents, in that the $NR^2R^3$ and/or the $R^4$ moieties are leaving groups susceptible to displacement by nucleophilic attack, e.g., by a hydroxyl or other group. For example, the compounds can be used to phosphitylate a nucleoside by reaction of a 3'-hydroxyl group or a 5'-hydroxyl group. The compounds are also useful for phosphitylating peptides and proteins, insofar as the compounds can phosphitylate an amino acid at any nucleophilic site, e.g., at the hydroxyl groups of serine, threonine and tyrosine, or at the sulfhydryl group of cysteine. Surprisingly, these compounds enable phosphitylation in very high yield. In one important application, the compounds provide the capability of sequentially synthesizing DNA oligonucleotides with very high coupling yields for each individual coupling reaction. The compounds of formula (I) may also be useful as therapeutic agents, and may be screened for activity using conventional techniques.

In another embodiment, modified nucleosides are provided having a phosphinoamidite carboxylate substituent, an H-phosphonite carboxylate substituent, or an analog thereof at either the 3' or the 5' position. The modified nucleosides have the structural formula (III)

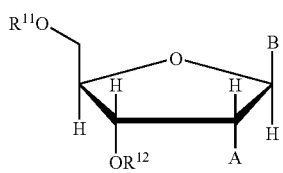

wherein: A is hydrogen, hydroxyl, lower alkoxy, lower alkoxy-substituted lower alkoxy, halogen, SH, $NH_2$, azide or DL wherein D is O, S or NH and L is a heteroatom-protecting group, unsubstituted hydrocarbyl, substituted hydrocarbyl, heteroatom-containing hydrocarbyl, or substituted heteroatom-containing hydrocarbyl; B is a nucleobase; and one of $R^{11}$ and $R^{12}$ is a blocking group and the other is (IV) or (VI)

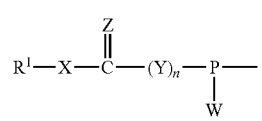

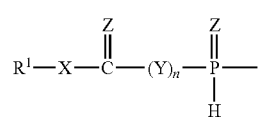

in which W is $NR^2R^3$, $NR^5R^6$ or DL, and $R^1$, X, Y, Z and n are as defined as follows: $R^1$ is hydrogen, a protecting group removable by an elimination reaction, hydrocarbyl, substituted hydrocarbyl, heteroatom-containing hydrocarbyl, or substituted heteroatom-containing hydrocarbyl; $R^2$ and $R^3$ are independently selected from the group consisting of hydrocarbyl, substituted hydrocarbyl, heteroatom-containing hydrocarbyl and substituted heteroatom-containing hydrocarbyl, or $R^2$ and $R^3$ are linked to form a substituted or unsubstituted, five- or six-membered nitrogen-containing heterocycle; $R^4$ is $NR^5R^6$, halogen or DL, wherein $R^5$ and $R^6$ are independently selected from the group consisting of hydrocarbyl, substituted hydrocarbyl, heteroatom-containing hydrocarbyl and substituted heteroatom-containing hydrocarbyl, or $R^5$ and $R^6$ are linked to form a substituted or unsubstituted, five- or six-membered nitrogen-containing heterocycle, D is O, S or NH, and L is a heteroatom-protecting group, unsubstituted hydrocarbyl, substituted hydrocarbyl, heteroatom-containing hydrocarbyl, or substituted heteroatom-containing hydrocarbyl; X is O, S NH or $NR^7$ wherein $R^7$ is hydrocarbyl, substituted hydrocarbyl, heteroatom-containing hydrocarbyl or substituted heteroatom-containing hydrocarbyl; n is zero or 1; Y is —$(Y')_m$—$(CR^8R^9)$— wherein m is zero or 1, Y' is hydrocarbylene, substituted hydrocarbylene, heteroatom-containing hydrocarbylene, or substituted heteroatom-containing hydrocarbylene, wherein $R^8$ and $R^9$ are as defined for $R^1$; and Z is O, S, NH or $NR^{10}$ wherein $R^{10}$ is as defined for $R^7$.

When the nucleoside contains moiety (IV), it is a nucleoside phosphinoamidite carboxylate or analog thereof, while when the nucleoside contains moiety (VI), it is a nucleoside H-phosphonite carboxylate or analog thereof.

In still another embodiment, modified oligonucleotides are provided that have reduced internucleotide charge at physiological pH and enhanced stability to degradation by nucleases. The modified oligonucleotides contain at least one internucleotide linkage having the structure of formula (VIII) or (X)

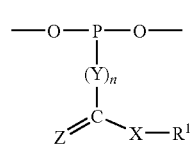

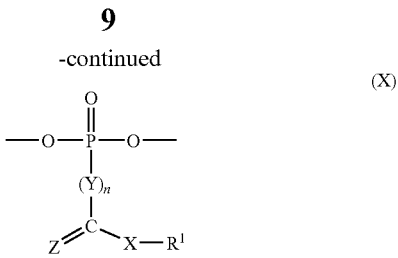

(X)

in which R¹, X, Y, Z and n are as defined above with respect to the modified nucleosides of formula (III), wherein when the internucleotide linkage is (VIII), the oligonucleotide is a "phosphinocarboxylate" oligonucleotide or analog thereof, while when the internucleotide linkage is (X), the oligonucleotide is a "phosphonocarboxylate" oligonucleotide or analog thereof. These phosphinocarboxylate and phosphonocarboxylate oligonucleotides find applications in a variety of areas, for example: as therapeutic agents, particularly as therapeutic agents in antisense-, ribozyme- and aptamer-based strategies; as diagnostic agents in target validation, to test selected proteins for suitability as a therapeutic target; in investigating the mechanism and stereochemistry of biochemical reactions; and in the mapping of nucleic acid protein interactions. Furthermore, since the novel oligonucleotides have unexpectedly been found to direct the hydrolysis of complementary RNA in the presence of RNaseH, they are also useful as agents for eliciting RNaseH activity. Finally, because the oligonucleotides have reduced charge relative to relative to oligonucleotides with standard phosphonate linkages, they readily pass through body membranes and in addition have enhanced utility in the area of mass spectrometry.

DETAILED DESCRIPTION OF THE INVENTION

I. Definitions and Overview

Figure 1:
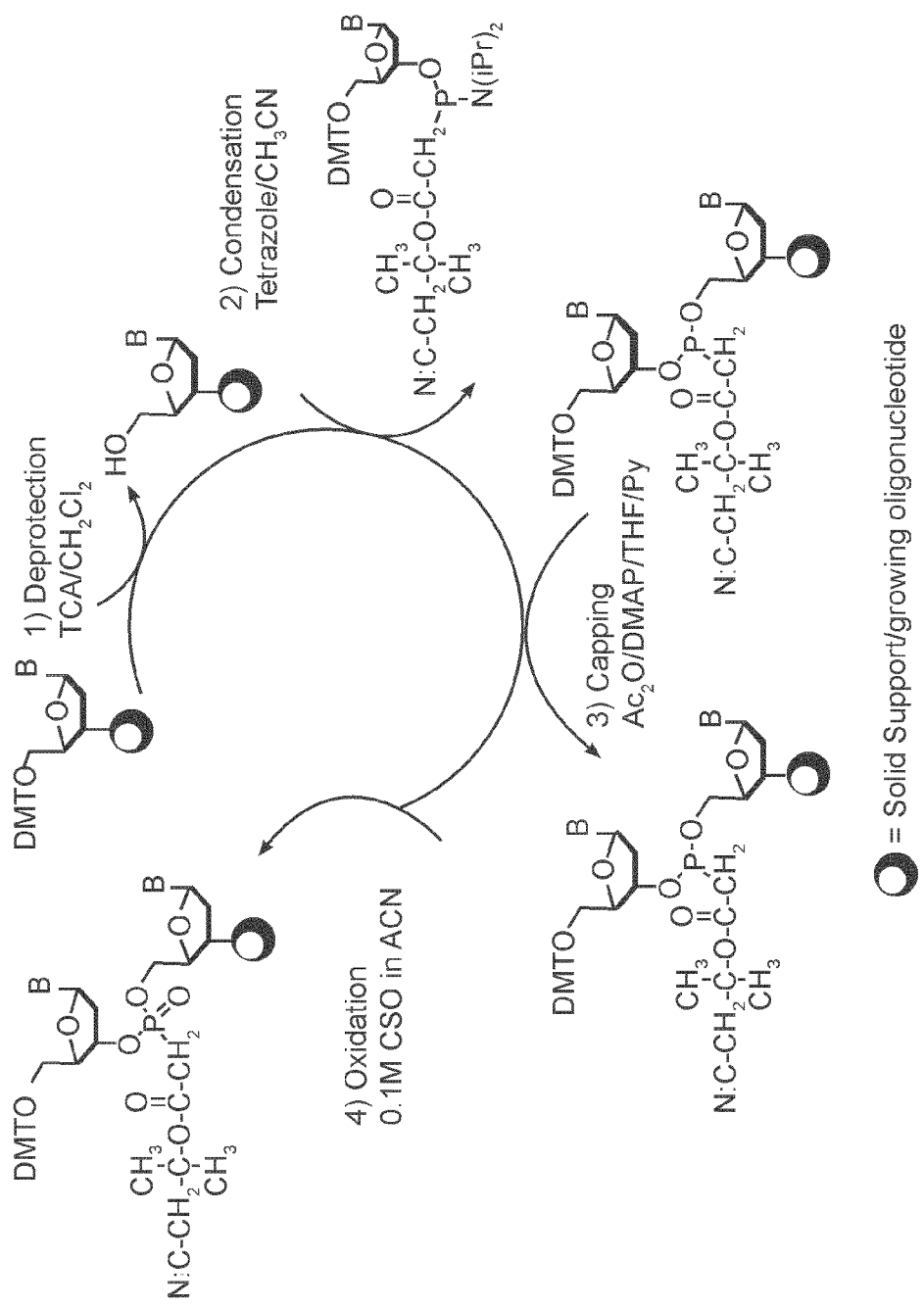
FIG. 1 schematically illustrates synthesis of phosphonoacetate polynucleotides on a solid support, as described in detail in Example 33.

Before describing the present invention in detail, it is to be understood that unless otherwise indicated this invention is not limited to specific compounds, reagents, reaction conditions, synthetic steps, or the like, as such may vary. It is also to be understood that the terminology used herein is for the purpose of describing particular embodiments only, and is not intended to be limiting.

It must be noted that, as used in the specification and the appended claims, the singular forms "a," "an" and "the" include plural referents unless the context clearly dictates otherwise. Thus, for example, reference to "a protecting group" includes combinations of protecting groups, reference to "a nucleoside" includes combinations of nucleosides, and the like. Similarly, reference to "a substituent" as in a compound substituted with "a substituent" includes the possibility of substitution with more than one substituent, wherein the substituents may be the same or different.

As used herein the symbols for nucleosides, nucleotides and polynucleotides are according to the IUPAC-IUB Commission of Biochemical Nomenclature recommendations (Biochemistry 9:4022 (1970)).

In this specification and in the claims which follow, reference will be made to a number of terms which shall be defined to have the following meanings:

As used herein, the phrase "having the structure" is not intended to be limiting and is used in the same way that the term "comprising" is commonly used. The term "independently selected from the group consisting of" is used herein to indicate that the recited elements, e.g., R groups or the like, can be identical or different.

"Optional" or "optionally" means that the subsequently described event or circumstance may or may not occur, and that the description includes instances where said event or circumstance occurs and instances where it does not. For example, the phrase "optionally substituted hydrocarbyl" means that a hydrocarbyl moiety may or may not be substituted and that the description includes both unsubstituted hydrocarbyl and hydrocarbyl where there is substitution.

The term "alkyl" as used herein refers to a branched or unbranched saturated hydrocarbon group typically although not necessarily containing 1 to about 20 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although again not necessarily, alkyl groups herein contain 1 to about 12 carbon atoms. The term "lower alkyl" intends an alkyl group of 1 to 6 carbon atoms, preferably 1 to 4 carbon atoms. "Substituted alkyl" refers to alkyl substituted with one or more substituent groups, and the terms "heteroatom-containing alkyl" and "heteroalkyl" refer to alkyl in which at least one carbon atom is replaced with a heteroatom. The term "cycloalkylalkyl" refers to an alkyl group substituted with a cycloalkyl substituent.

The term "alkylene" as used herein refers to difunctional, branched or unbranched saturated hydrocarbon group typically although not necessarily containing 1 to about 20 carbon atoms, such as methylene, ethylene, n-propylene, n-hexylene, methylethylene, and the like. Generally, although again not necessarily, alkylene groups herein contain 1 to about 12 carbon atoms. The term "lower alkylene" intends an alkylene group of 1 to 6 carbon atoms, preferably 1 to 4 carbon atoms. "Substituted alkylene" refers to alkylene substituted with one or more substituent groups, and the terms "heteroatom-containing alkylene" and "heteroalkylene" refer to alkylene in which at least one carbon atom is replaced with a heteroatom.

The term "alkenyl" as used herein refers to a branched or unbranched hydrocarbon group typically although not necessarily containing 2 to about 20 carbon atoms and at least one double bond, such as ethenyl, n-propenyl, isopropenyl, s-propenyl, 2-propenyl, n-butenyl, isobutenyl, octenyl, decenyl, and the like. Generally, although again not necessarily, alkenyl groups herein contain 3 to about 10 carbon atoms. The term "lower alkenyl" intends an alkenyl group of 2 to 6 carbon atoms, preferably 2 to 4 carbon atoms. "Substituted alkenyl" refers to alkenyl substituted with one or more substituent groups, and the terms "heteroatom-containing alkenyl" and "heteroalkenyl" refer to alkenyl in which at least one carbon atom is replaced with a heteroatom.

The term "alkynyl" as used herein refers to a branched or unbranched hydrocarbon group typically although not necessarily containing 2 to about 20 carbon atoms and at least one triple bond, such as ethynyl, n-propynyl, n-butynyl, octynyl, decynyl, and the like. Generally, although again not necessarily, alkynyl groups herein contain 3 to about 10 carbon atoms. The term "lower alkynyl" intends an alkynyl group of 2 to 6 carbon atoms, preferably 2, 3 or 4 carbon atoms. "Substituted alkynyl" refers to alkynyl substituted with one or more substituent groups, and the terms "heteroatom-containing alkynyl" and "heteroalkynyl" refer to alkynyl in which at least one carbon atom is replaced with a heteroatom.

The term "alkoxy" as used herein intends an alkyl group bound through a single, terminal ether linkage; that is, an "alkoxy" group may be represented as —O-alkyl where alkyl is as defined above. A "lower alkoxy" group intends an alkoxy group containing 1 to 6, more preferably 1 to 4, carbon atoms.

The term "amino" is used herein to refer to the —NH$_2$ group, while "substituted amino" refers to —NHZ$^1$ and —NZ$^1$Z$^2$ groups, where each of Z$^1$ and Z$^2$ is independently selected from the group consisting of optionally substituted hydrocarbyl and heteroatom-containing hydrocarbyl, or wherein, in disubstituted amino groups, Z$^1$ and Z$^2$ may be linked to form an optionally substituted hydrocarbylene or heteroatom-containing hydrocarbylene bridge.

The term "aryl" as used herein, and unless otherwise specified, refers to an aromatic substituent containing a single aromatic ring or multiple aromatic rings that are fused together, linked covalently, or linked to a common group such as a methylene or ethylene moiety. The common linking group may also be a carbonyl as in benzophenone, an oxygen atom as in diphenylether, or a nitrogen atom as in diphenylamine. Preferred aryl groups contain one aromatic ring or two fused or linked aromatic rings, e.g., phenyl, naphthyl, biphenyl, diphenylether, diphenylamine, benzophenone, and the like. "Substituted aryl" refers to an aryl moiety substituted with one or more substituent groups, and the terms "heteroatom-containing aryl" and "heteroaryl" refer to aryl in which at least one carbon atom is replaced with a heteroatom.

The term "arylene" as used herein, and unless otherwise specified, refers to a divalent aromatic substituent containing a single aromatic ring or multiple aromatic rings that are fused together or linked covalently. Preferred arylene groups contain one aromatic ring or two fused or linked aromatic rings. "Substituted arylene" refers to an arylene moiety substituted with one or more substituent groups, and the terms "heteroatom-containing arylene" and "heteroarylene" refer to arylene in which at least one carbon atom is replaced with a heteroatom.

The term "aralkyl" refers to an alkyl group with an aryl substituent, the term "aralkenyl" refers to an alkenyl group with an aryl substituent, the term "aralkynyl" refers to an alkynyl group with an aryl substituent, and the term "aralkylene" refers to an alkylene group with an aryl substituent. The term "alkaryl" refers to an aryl group that has an alkyl substituent, the term "cycloalkylaryl" refers to an aryl group that has a cycloalkyl substituent, and the term "alkarylene" refers to an arylene group with an alkyl substituent.

The terms "halo" and "halogen" are used in the conventional sense to refer to a chloro, bromo, fluoro or iodo substituent. The terms "haloalkyl," "haloalkenyl" or "haloalkynyl" (or "halogenated alkyl," "halogenated alkenyl," "halogenated aromatic" or "halogenated alkynyl") refers to an alkyl, alkenyl, aromatic or alkynyl group, respectively, in which at least one of the hydrogen atoms in the group has been replaced with a halogen atom.

The term "heteroatom-containing" as in a "heteroatom-containing hydrocarbyl group" refers to a molecule or molecular fragment in which one or more carbon atoms is replaced with an atom other than carbon, e.g., nitrogen, oxygen, sulfur or phosphorus. Similarly, the term "heteroalkyl" refers to an alkyl substituent that is heteroatom-containing, the term "heterocyclic" refers to a cyclic substituent that is heteroatom-containing, the term "heteroaryl" refers to an aryl substituent that is heteroatom-containing, and the like. Heteroatoms can also replace certain carbon atoms as part of unsaturated systems such as wherein an oxygen atom replaces a carbon atom in an alkene to generate a ketone or aldehyde, and wherein a nitrogen atom replaces a carbon atom in an alkyne to generate a nitrile. Examples of common heteroatom-substituted radicals used in nucleotide chemistry are β-cyanoethyl, methyl-β-cyanoethyl, dimethyl-β-cyanoethyl, phenylsulfonylethyl, methyl-sulfonylethyl, p-nitrophenylsulfonylethyl, 2,2,2-trichloro-1,1-dimethylethyl, 2-(4-pyridyl)ethyl, 2-(2-pyridyl)ethyl, -thiobenzoylethyl, 1,1,1,3,3,3-hexafluoro-2-propyl, 2,2,2-trichloroethyl, p-nitrophenylethyl, p-cyanophenylethyl, acetyl, tetrahydropyranyl, di-p-methoxytrityl, and benzoyl radicals. When the term "heteroatom-containing" appears prior to a list of possible heteroatom-containing groups, it is intended that the term apply to every member of that group.

"Hydrocarbyl" refers to univalent hydrocarbyl radicals containing 1 to about 30 carbon atoms, preferably 1 to about 20 carbon atoms, most preferably 1 to about 12 carbon atoms, including branched or unbranched, saturated or unsaturated species, such as alkyl groups, alkenyl groups, aryl groups, and the like. The term "lower hydrocarbyl" intends a hydrocarbyl group of 1 to 6 carbon atoms, preferably 1 to 4 carbon atoms. The term "hydrocarbylene" intends a divalent hydrocarbyl moiety containing 1 to about 30 carbon atoms, preferably 1 to about 24 carbon atoms, most preferably 1 to about 12 carbon atoms, including branched or unbranched, saturated or unsaturated species, or the like. The term "lower hydrocarbylene" intends a hydrocarbylene group of one to six carbon atoms, preferably one to four carbon atoms. "Substituted hydrocarbyl" refers to hydrocarbyl substituted with one or more substituent groups, and the terms "heteroatom-containing hydrocarbyl" and "heterohydrocarbyl" refer to hydrocarbyl in which at least one carbon atom is replaced with a heteroatom. Similarly, "substituted hydrocarbylene" refers to hydrocarbylene substituted with one or more substituent groups, and the terms "heteroatom-containing hydrocarbylene" and "heterohydrocarbylene" refer to hydrocarbylene in which at least one carbon atom is replaced with a heteroatom.

The term "phosphoryl" as in a "phosphoryl group" refers to a pendent phosphorus-containing moiety, protected or unprotected, modified or unmodified.

The term "phosphinocarboxylate" refers to the group

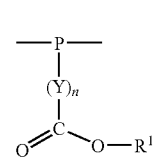

while the term "phosphonocarboxylate" refers to the group

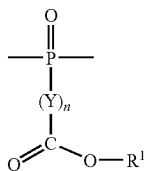

and the term "H-phosphonite carboxylate" refers to the group

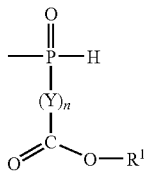

wherein n, Y and $R^1$ are as defined previously. The term "analogs" of phosphinocarboxylates, phosphonocarboxylates and H-phosphonite carboxylates refers to moieties wherein either or both of the oxygen atoms in the carboxylate moiety are replaced with another atom, e.g., S or N, and/or wherein the carboxylate is in the form of a carboxylic acid ($R^1$ is H) or a carboxylic acid salt in which a carboxylic acid anion $COO^-$ is associated with a cationic counterion. When the term "analog" is not explicitly used, it should be understood that "carboxylate" as used herein refers not only to the group

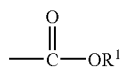

but also to the groups

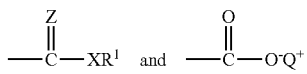

wherein $R^1$, X and Z are as defined previously, and Q is a cationic counterion that may be either organic or inorganic, e.g., a metal ion, an ammonium ion, or the like.

By "substituted" as in "substituted hydrocarbyl," "substituted hydrocarbylene," "substituted alkyl," and the like, as alluded to in some of the aforementioned definitions, is meant that in the hydrocarbyl, hydrocarbylene, alkyl, alkenyl or other moiety, at least one hydrogen atom bound to a carbon atom is replaced with one or more substituents that are functional groups such as hydroxyl, alkoxy, thio, amino, halo, and the like. When the term "substituted" appears prior to a list of possible substituted groups, it is intended that the term apply to every member of that group.

It will be appreciated that, as used herein, the terms "nucleobase," "nucleoside" and "nucleotide" refer to nucleobases, nucleosides and nucleotides containing not only the conventional purine and pyrimidine bases, i.e., adenine (A), thymine (T), cytosine (C), guanine (G) and uracil (U), but also protected forms thereof, e.g., wherein the base is protected with a protecting group such as acetyl, difluoroacetyl, trifluoroacetyl, isobutyryl or benzoyl, and purine and pyrimidine analogs. Where the term "nucleobase" is used, therefore, the term includes unprotected and protected nucleosides and nucleotides or analogs thereof. Suitable analogs will be known to those skilled in the art and are described in the pertinent texts and literature. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. Unless otherwise indicated, the term "nucleoside" is also intended to encompass nucleoside monomers as well as nucleosides present within an oligonucleotide chain, either at a terminus thereof or within the oligonucleotide backbone.

As used herein, the term "oligonucleotide" shall be generic to polydeoxynucleotides (containing 2-deoxy-D-ribose), to polyribonucleotides (containing D-ribose), to any other type of polynucleotide which is an N-glycoside of a purine or pyrimidine base, and to other polymers containing non-nucleotidic backbones, providing that the polymers contain nucleobases in a configuration which allows for base pairing and base stacking, such as is found in DNA and RNA. The term "oligonucleotide" includes double- and single-stranded DNA, as well as double- and single-stranded RNA and DNA: RNA hybrids, and also include known types of modifications, for example, labels which are known in the art, methylation, "caps," and the like. The oligonucleotides may be naturally occurring or chemically synthesized.

The term "protecting group" as used herein is meant a species that prevents a segment of a molecule from undergoing a specific chemical reaction, but which is removable from the molecule following completion of that reaction. This is in contrast to a "capping group" which permanently binds to a segment of a molecule to prevent any further chemical transformation of that segment.

The term "blocking group" as used herein is meant a species which prevents a segment of a molecule from undergoing a specific chemical reaction, but which may or may not be removable from the molecule following completion of that reaction. An example, by way of illustration and not limitation, of a blocking group that may or may not be removable from the molecule is a methyl ester of a carboxylic acid. A methyl ester of a carboxylic acid may be removed from the molecule to form an acidic functional group that under certain pH conditions gives the molecule a negative charge, or may be left on the molecule to neutralize a resulting charge. It will be appreciated that, as used herein, the term "blocking group" can also refer to any atom or molecule which may prevent a specific chemical reaction from occurring at that segment of the molecule. It should be noted that the term "blocking group" as used herein is intended to encompass "protecting groups" as defined above. Greene and Wuts, *Protective Groups in Organic Synthesis,* 2nd Edition (John Wiley, New York, 1991) provides extensive guidance on the selection of removable blocking groups (i.e., protecting groups) for use herein.

The term "electron withdrawing" denotes the tendency of a substituent to attract valence electrons of the molecule of which it is a part, i.e., an electron-withdrawing substituent is electronegative.

The term "elimination reaction" as used herein is meant to describe a chemical reaction by which a species is removed by "elimination" or "fragmentation." This is in contrast to an operation by which a species is removed by a "substitution reaction." An example of this distinction is the contrast between the typical method for the removal of an ethyl group from a protected carboxylic acid (i.e., an ethyl ester) using a hydroxide nucleophile, and the removal of a β-cyanoethyl blocking group from a protected carboxylic acid (i.e., a β-cyanoethyl ester) using a non-nucleophilic base. The ethyl-protected carboxylic acid is deprotected by substitution of the ethoxide group on the carbonyl group of the ester with hydroxide, whereas the β-cyanoethyl-protected carboxylic acid is deprotected by elimination or fragmentation as the protecting group is transformed by specific chemical reactions leaving the carboxylate intact. With the β-cyanoethyl protecting group, the specific chemical reaction is base-catalyzed β-elimination. There are many other protecting groups, well known to those skilled in the art, which may be removed by elimination or fragmentation, leaving the carboxylate moiety intact, rather than by substitution on the carbonyl. Examples of protecting groups that may be removed by elimination reactions, by way of illustration and not limitation, are: β-cyanoethyl, methyl-β-cyanoethyl, dimethyl-β-cyanoethyl, phenylsulfonylethyl, methyl-sulfonylethyl, p-nitrophenylsulfonylethyl, 2,2,2-trichloro-1,1-dimethylethyl, 2-(4-pyridyl)ethyl, 2-(2-pyridyl)ethyl, allyl, 4-methylene-1-acetylphenol, -thiobenzoylethyl, 1,1,1,3,3,3-hexafluoro-2-propyl, 2,2,2-trichloroethyl, p-nitrophenylethyl, p-cyanophenyl-ethyl, 9-fluorenylmethyl, 1,3-dithionyl-2-methyl, 2-(trimethylsily)ethyl, 2-methylthioethyl, 2-(diphenylphosphino)-ethyl, 1-methyl-1-phenylethyl, 3-buten-1-yl, 4-(trimethylsilyl)-2-buten-1-yl, cinnamyl, -methylcinnamyl, and 8-quinolyl.

The terms "substrate," "surface" and "solid phase" refer to any structure that can be used to physically separate reactions or reaction products from reactants, starting materials, and/or by-products. Suitable substrate materials include, but are not limited to, supports that are typically used for solid phase chemical synthesis, e.g., polymeric materials, silica and silica-based materials, glasses, ceramics, metals, and the like. In some embodiments, the substrate surface will be substantially flat although in other embodiments highly porous materials or microbeads will be utilized.

"Optional" or "optionally" means that the subsequently described circumstance may or may not occur, so that the description includes instances where the circumstance occurs and instances where it does not. For example, recitation of a substituent as "optionally present" encompasses both the molecular moiety containing the substituent and the molecular moiety not containing the substituent.

In the molecular structures herein, single bonds are indicated in the conventional sense using a single line connecting two atoms, while double bonds are indicated in the conventional sense using a double line between two adjacent atoms. However, it will be appreciated that molecular structures can be drawn in different ways, and that in some cases a particular bond may be drawn as either a single or double bond, with both representations being chemically accurate and indicating the same structure.

It should also be emphasized that certain molecular entities or molecular segments herein may contain one or more chiral centers and thus may be a racemic mixture (50-50) of isomers, a mixture of isomers where one isomer is present in excess, or a substantially pure isomer, "substantially pure" meaning that one isomer represents greater than 90%, preferably greater than 95%, more preferably greater than 99%, of a mixture of isomers. It is intended that for such chiral molecules the disclosure herein encompasses a mixture of isomers as well as a substantially pure isomer.

II. Phosphinoamidite Carboxylates and Analogs Thereof

This present invention relates in part to novel phosphorus-containing compounds that are particularly useful for making phosphonocarboxylate mimics of naturally occurring, biologically active, nucleoside and oligonucleotide phosphonates. The novel compounds, phosphinoamidite carboxylates and analogs thereof, are especially useful for the preparation of protected nucleoside phosphinocarboxylates, which in turn enable formation of phosphinocarboxylate and phosphonocarboxylate internucleotide bonds, and for the first time allow for the synthesis of phosphinocarboxylate and phosphonocarboxylate oligonucleotides and polynucleotides. That is, these highly reactive P(III) derivatives enable the synthesis of phosphinocarboxylate and phosphonocarboxylate oligonucleotides through the high yielding formation of phosphinocarboxylate and phosphonocarboxylate internucleotide bonds. Generally, the phosphinoamidite carboxylates will have the carboxylate functional group protected with a blocking group that is removable using elimination or fragmentation reactions. These blocking groups undergo quantitative deprotection reactions under conditions that leave the phosphorus-carboxylate moiety intact. These novel phosphinoamidite carboxylates also enable the synthesis of new nucleoside H-phosphonite carboxylates as well as phosphinocarboxylate-derived and phosphonocarboxylate-derived amino acids, peptides, proteins and carbohydrates.

In one embodiment, then, phosphinoamidite carboxylates and analogs thereof are provided having the structure of formula (I)

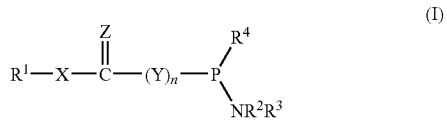

(I)

wherein the various substituents are as follows:

$R^1$ is hydrogen, a protecting group removable by an elimination reaction, hydrocarbyl, substituted hydrocarbyl, heteroatom-containing hydrocarbyl or substituted heteroatom-containing hydrocarbyl. Preferably, $R^1$ is hydrogen or an unsubstituted, substituted, heteroatom-containing or substituted heteroatom-containing moiety selected from the group consisting of alkyl, aryl, aralkyl, alkaryl, cycloalkyl, cycloalkylalkyl, cycloalkylaryl, alkenyl, cycloalkenyl, aralkenyl, alkynyl and aralkynyl. $R^1$ may also be a protecting group, in which case it is removable by an elimination reaction. Protecting groups suitable for use as $R^1$ will generally although not necessarily be: electron-withdrawing-substituted aliphatic groups, particularly electron-withdrawing-substituted ethyl; electron-withdrawing substituted phenyl; and electron-withdrawing substituted phenylethyl. Specific examples of suitable protecting groups include, by way of example, β-cyanoethyl, methyl-β-cyanoethyl, dimethyl-β-cyanoethyl, phenylsulfonylethyl, methyl-sulfonylethyl, p-nitrophenylsulfonylethyl, 2,2,2-trichloro-1,1-dimethylethyl, 2-(4-pyridyl)ethyl, 2-(2-pyridyl)ethyl, allyl, 4-methylene-1-acetylphenol, -thiobenzoylethyl, 1,1,1,3,3,3-hexafluoro-2-propyl, 2,2,2-trichloroethyl, p-nitrophenylethyl, p-cyanophenyl-ethyl, 9-fluorenylmethyl, 1,3-dithionyl-2-methyl, 2-(trimethylsilyl)ethyl, 2-methylthioethyl, 2-(diphenylphosphino)ethyl, 1-methyl-1-phenylethyl, 3-buten-1-yl, 4-(trimethylsilyl)-2-buten-1-yl, cinnamyl, -methylcinnamyl, and 8-quinolyl.

$R^2$ and $R^3$ are independently selected from the group consisting of hydrocarbyl, substituted hydrocarbyl, heteroatom-containing hydrocarbyl and substituted heteroatom-containing hydrocarbyl. Preferably, $R^2$ and $R^3$ are unsubstituted, substituted, heteroatom-containing or substituted heteroatom-containing moieties selected from the group consisting of alkyl, aryl, aralkyl, alkaryl, cycloalkyl, cycloalkylalkyl, cycloalkylaryl, alkenyl, cycloalkenyl, alkynyl and aralkynyl. That is, $R^2$ and $R^3$ may be the same or different and are typically selected from the group consisting of alkyl, aryl, aralkyl, alkaryl, cycloalkyl, alkenyl, cycloalkenyl, alkynyl, cycloalkynyl, optionally containing one or more nonhydrocarbyl linkages such as ether linkages, thioether linkages, oxo linkages, amine and imine linkages, and optionally substituted on one or more available carbon atoms with a nonhydrocarbyl substituent such as cyano, nitro, halo, or the like. Preferably, $R^2$ and $R^3$ represent lower alkyl, more preferably sterically hindered lower alkyls such as isopropyl, t-butyl, isobutyl, sec-butyl, neopentyl, tert-pentyl, isopentyl, sec-pentyl, and the like. Most preferably, $R^2$ and $R^3$ both represent isopropyl. Alternatively, $R^2$ and $R^3$ are linked to form a mono- or polyheterocyclic ring having a total of from 1 to 3, usually 1 to 2 heteroatoms and from 1 to 3 rings. In such a case, $R^2$ and $R^3$ together with the nitrogen atom to which they are attached represent, for example, pyrrolidino, morpholino, piperazino or piperidino. Usually, $R^2$ and $R^3$ have a total of from 2 to 12 carbon atoms. Correspondingly preferred $NR^2R^3$ groups include, without limitation, dimethylamino, diethylamino, diisopropylamino, dibutylamino, methylpropylamino, methylhexylamino, methylcyclohexylamino, ethylcyclopropyl-amino, ethylchloroethylamino, methylbenzylamino, methylphenylamino, thiomorpholino, methyltoluylamino, methyl-p-chlorophenylamino, methylcyclohexylamino, bromobutylcyclohexylamino, methyl-p-cyanophenylamino, ethyl-β-cyanoethylamino, piperidino, 2,6-dimethylpiperidino, pyrrolidino, piperazino, isopropylcyclohexylamino, and morpholine. An exemplary $NR^2R^3$ group is diisopropylamino.

$R^4$ is $NR^5R^6$, halogen or DL, wherein $R^5$ and $R^6$ are as defined above for $R^2$ and $R^3$, D is O, S or NH, preferably O, and L is a heteroatom-protecting group, unsubstituted hydrocarbyl, substituted hydrocarbyl, heteroatom-containing hydrocarbyl, or substituted heteroatom-containing hydrocarbyl. When L is a heteroatom-protecting group, it is removable by an elimination reaction. Examples of heteroatom-protecting groups that can serve as L include, but are not limited to, those groups recited as suitable $R^1$ protecting groups that are removable by an elimination reaction, i.e. β-cyanoethyl, methyl-β-cyanoethyl, dimethyl-β-cyanoethyl, phenylsulfonylethyl, methyl-sulfonylethyl, p-nitrophenyl-sulfonylethyl, 2,2,2-trichloro-1,1-dimethylethyl, 2-(4-pyridyl)ethyl, 2-(2-pyridyl)ethyl, allyl, 4-methylene-1-acetylphenol, -thiobenzoylethyl, 1,1,1,3,3,3-hexafluoro-2-propyl, 2,2,2-trichloroethyl, p-nitrophenylethyl, p-cyanophenyl-ethyl, 9-fluorenylmethyl, 1,3-dithionyl-2-methyl, 2-(trimethylsilyl)ethyl, 2-methylthioethyl, 2-(diphenylphosphino)ethyl, 1-methyl-1-phenylethyl, 3-buten-1-yl, 4-(trimethylsilyl)-2-buten-1-yl, cinnamyl, -methylcinnamyl and 8-quinolyl.

X is O, S, NH or $NR^7$, wherein $R^7$ is hydrocarbyl, substituted hydrocarbyl, heteroatom-containing hydrocarbyl or substituted heteroatom-containing hydrocarbyl, preferably unsubstituted, substituted, heteroatom-containing or substituted heteroatom-containing moieties selected from the group consisting of alkyl, aryl, aralkyl, alkaryl, cycloalkyl, cycloalkylalkyl, cycloalkylaryl, alkenyl, cycloalkenyl, alkynyl and aralkynyl. Generally, however, X is O.

The subscript "n" is zero or 1, meaning that the linkage Y may or may not be present. If present, Y is $-(Y')_m-(CR^8R^9)-$ wherein m is zero or 1, Y' is hydrocarbylene, substituted hydrocarbylene, heteroatom-containing hydrocarbylene, or substituted heteroatom-containing hydrocarbylene, wherein $R^8$ and $R^9$ are independently selected from the group consisting of hydrogen, hydrocarbyl, substituted hydrocarbyl, heteroatom-containing hydrocarbyl and substituted heteroatom-containing hydrocarbyl, with the proviso that when n is 1, m is zero and $R^8$ and $R^9$ are both hydrogen, then $R^1$ is hydrogen or a protecting group removable by an elimination reaction. Preferably, $R^8$ and $R^9$ are hydrogen or unsubstituted, substituted, heteroatom-containing or substituted heteroatom-containing moieties selected from the group consisting of alkyl, aryl, aralkyl, alkaryl, cycloalkyl, cycloalkylalkyl, cycloalkylaryl, alkenyl, cycloalkenyl, alkynyl and aralkynyl. Optimally, either n is zero or n is 1 and m is 1.

Z is O, S, NH or $NR^{10}$ wherein $R^{10}$ is as defined for $R^7$. Generally and preferably, however, Z is O.

It should also be noted that if $NR^2R^3$ is not the same as $R^4$, the compound of formula (I) is a chiral molecule that can exist in one of two isomeric forms, i.e., as

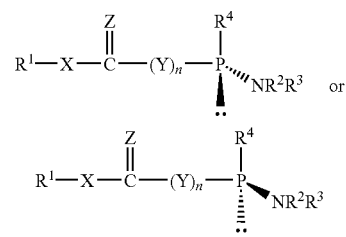

These two isomers are readily separated using conventional means, e.g., chromatographic means such as TLC or HPLC. The compounds can thus be used to prepare stereoisomerically pure modified nucleosides, oligonucleotides, and other compounds. See, for example, Wilk et al. (2000) *J. Am. Chem. Soc.* 122:2149-2156.

In a particularly preferred embodiment, then, the phosphinoamidite carboxylate has the structure of formula (II)

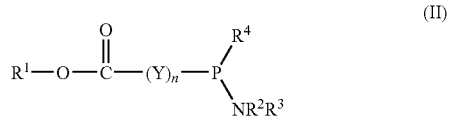

(II)

wherein; $R^1$ is hydrogen, lower alkyl, or a hydroxyl-protecting group removable by an elimination reaction, preferably although not necessarily an electron-withdrawing-substituted aliphatic group; $R^2$ and $R^3$ are lower alkyl, e.g., isopropyl, or $R^2$ and $R^3$ are linked to form a piperidino, piperazino or morpholino ring; $R^4$ is $NR^5R^6$, chloro or OL wherein $R^5$ and $R^6$ are as defined for $R^2$ and $R^3$, and L is a hydroxyl-protecting group removable by an elimination reaction, generally although not necessarily selected from the group consisting of β-cyanoethyl, methyl-β-cyanoethyl, dimethyl-β-cyanoethyl, phenylsulfonylethyl, methylsulfonylethyl, p-nitrophenyl-sulfonylethyl, 2,2,2-trichloro-1,1-dimethylethyl, 2-(4-pyridyl)ethyl, 2-(2-pyridyl)ethyl, allyl, 4-methylene-1-acetylphenol, -thiobenzoylethyl, 1,1,1,3,3,3-hexafluoro-2-propyl, 2,2,2-trichloroethyl, p-nitrophenylethyl, p-cyanophenyl-ethyl, 9-fluorenylmethyl, 1,3-dithionyl-2-methyl, 2-(trimethylsilyl)ethyl, 2-methylthioethyl, 2-(diphenylphosphino)ethyl, 1-methyl-1-phenylethyl, 3-buten-1-yl, 4-(trimethylsilyl)-2-buten-1-yl, cinnamyl, -methylcinnamyl and 8-quinolyl; n is zero or 1; and Y is $-(Y')_m-(CH_2)-$ wherein m is zero or 1 and Y' is lower alkylene, with the proviso that when n is 1 and m is zero, then $R^1$ is either hydrogen or a hydroxyl-protecting group.

These phosphinoamidite carboxylates and analogs thereof may be readily synthesized from a commercially available phosphorus trihalide such as phosphorus trichloride by reaction with a secondary amine $NHR^2R^3$, wherein $R^2$ and $R^3$ are as defined earlier. The reaction may be controlled to produce the desired mono-substituted or di-substituted reaction product by the stoichiometric addition of the secondary amine. Alternatively, an $NR^5R^6$ moiety or a DL moiety may be introduced along with an $NR^2R^3$ moiety by reaction of the phosphorus trihalide with one equivalent of $NHR^2R^3$ and one equivalent of either $HNR^5R^6$ or H-DL, wherein $R^5$, $R^6$, D and L are as defined earlier. Depending on the selected reactants and the quantities used in the reaction, then, the phosphorus amide halide so produced has the structure

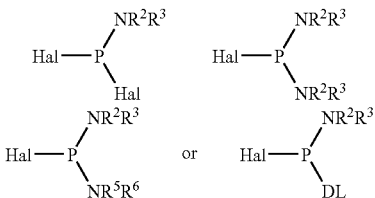

wherein Hal is halogen, e.g., chloro. One specific example of such a reaction employs phosphorus trichloride and diisopropyl amine, which react to produce bis-N,N-diisopropylamino chlorophosphine. The product of the reaction may be isolated and purified by vacuum distillation, recrystallization, or other techniques. The reaction of chlorophosphines with dialkyl amines has been described and is well known to those skilled in the art (Schwarz et al. (1984) *Tetrahedron Lett.* 25:5513; Dahl et al. (1987) *Nucleosides & Nucleotides* 6:457; Mcbride et al. (1983) *Tetrahedron Lett.* 24:245). The phosphorus amide halide may then be converted to the phosphinoamidite carboxylate by reaction with a suitably substituted carboxylate or analog thereof, e.g.,

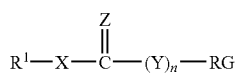

wherein $R^1$, X, Y, Z and n are as defined previously, and RG is a reactive group that is displaced upon reaction with the phosphorus amide halide.

Compounds of formula (I) are useful as phosphitylating agents, in that the $NR^2R^3$ and/or the $R^4$ moieties are leaving groups susceptible to displacement by nucleophilic attack, e.g., by a hydroxyl or other group. For example, the compounds can be used to phosphitylate a nucleoside or an oligonucleotide by reaction of a 3'-hydroxyl group, as follows:

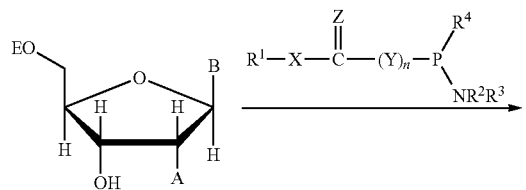

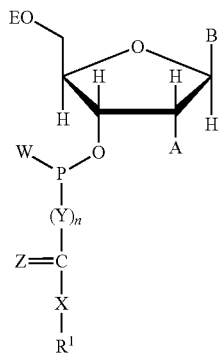

In the example illustrated, A is generally H or a protected hydroxyl group, B is a nucleobase, which may be protected with one or more protecting groups as known in the art, E is hydrogen, a suitable 3'-hydroxyl protecting group, or a continuing oligonucleotide chain, $R^4$ is $NR^5R^6$, halogen or DL, and W is $NR^2R^3$, $NR^5R^6$ or DL. Typically, the reaction conditions for this phosphitylation reaction are the same as those used in known methods of DNA synthesis, e.g., using conventional phosphoramidite chemistry (see Beaucage and Caruthers (1981) *Tetrahedron Lett.* 22:1859-1862). It should be noted that the substituent W in the phosphitylated product is determined by $R^4$ in the phosphitylating reagent. That is, when $R^4$ is halogen, e.g., chloro, W will be $NR^2R^3$. When $R^4$ is DL, then W will generally be DL, unless DL and $NR^2R^3$ are selected such that DL is a better leaving group than $NR^2R^3$. When $R^4$ is $NR^5R^6$, then W will be $NR^2R^3$ or $NR^5R^6$, or there may be a mixture of reaction products wherein W is $NR^2R^3$ or $NR^5R^6$, again, the substituent in the reaction may be controlled by appropriate selection of $R^2$, $R^3$, $R^5$ and $R^6$ as will be appreciated by those skilled in the art.

Generally, when the compounds of formula (I) are used to phosphitylate a nucleoside or an oligonucleotide, protecting groups (e.g., amine-protecting groups) are used to protect the nucleobase "B." Nucleobase protecting groups and methods for protecting and deprotecting nucleobases are known in the art and described in the pertinent texts and literature, e.g.: Shaller et. al. (1963) *J. Am Chem Soc.* 85: 3821; Ti et. al. (1982) *J. Am. Chem. Soc.* 104: 1316; Chaix et. al. (1989) *Tetrahedron Lett.* 30:71; Hagen et. al. (1989) *J. Org. Chem.* 54:3189; Nyilas et. al. (1988) *Nucleosides & Nucleotides* 7:787; Himmelsbach et. al. (1983) *Tetrahedron Lett.* 24: 3583; McBride et. al. (1986) *J. Am. Chem. Soc.* 108: 2040; and Beijer et. al. (1990) *Nucl. Acids Res.* 18:5143.

Peptides, proteins and individual amino acids may also be phosphitylated using the phosphitylating agents of formula (I) at any nucleophilic site, e.g., at the hydroxyl groups of serine, threonine and tyrosine, or at the sulfhydryl group of cysteine. It should be emphasized, however, that the phosphitylating agents of formula (I) are not limited with respect to use in phosphitylating biomolecules such as nucleosides, oligonucleotides, peptides, proteins and amino acids, but are useful in phosphitylating any compounds having a nucleophilic site that can displace the $NR^2R^3$ or $R^4$ moieties bound to the phosphorus atom of the phosphitylating agent.

The compounds of formula (I) may also be useful as therapeutic agents, e.g., as antiviral agents or anticancer agents, and may be screened for activity using conventional techniques. Compounds of formula (I) having antiviral activity may be used to treat a patient afflicted with a viral infection. Viral infections include, by way of example: retroviruses such as, but not limited to, HTLV-I, HTLV-II, human immunodeficiency viruses, HTLV-III (AIDS virus), and the like; RNA viruses such as, but not limited to, influenza type A, B, and C, mumps, measles, rhinovirus, dengue, rubella, rabies, hepatitis virus A, encephalitis virus, and the like; and DNA viruses such as, but not limited to, herpes viruses (including herpes simplex virus-1, herpes simplex virus-2, varicella-zoster virus, Epstein-Barr virus, human cytomegalovirus, human herpes virus 6, human herpes virus 7, and human herpes virus 8), vaccinia, papilloma virus, hepatitis virus B, and the like. Compounds of formula (I) having anticancer activity may be used to treat a patient afflicted with or susceptible to a neoplastic disease state. Neoplastic disease states include: leukemias such as, but not limited to, acute lymphoblastic, chronic lymphocytic, acute myloblastic and chronic mylocytic leukemias; carcinomas, such as, but not limited to, those of the cervix, oesophagus, stomach, small intestines, colon and lungs; sarcomas, such as, but not limited to, oesteroma, osteosarcoma, lepoma, liposarcoma, hemangioma and hemangiosarcoma; melanomas, including amelanotic and melanotic; and mixed types of neoplasias such as, but not limited to, carcinosarcoma, lymphoid tissue type, follicular reticulum, cell sarcoma and Hodgkins Disease.

III. Nucleoside Phosphinoamidite Carboxylates and Nucleoside H-Phosphonite Carboxylates In another embodiment of the invention, nucleoside phosphinoamidite carboxylates, nucleoside H-phosphonite carboxylates, and analogs thereof are provided. The nucleoside phosphinoamidite carboxylates and analogs thereof have the structural formula (III)

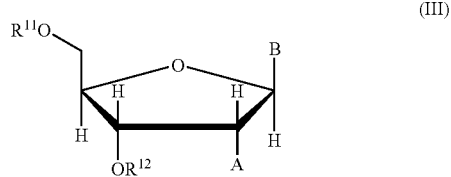

(III)

wherein the various substituents are as follows:

A is hydrogen, hydroxyl, halogen, tower alkoxy, lower alkoxy-substituted lower alkoxy, SH, $NH_2$, azide or DL wherein D is O, S or NH and L is as defined previously, i.e., a heteroatom-protecting group, unsubstituted hydrocarbyl, substituted hydrocarbyl, heteroatom-containing hydrocarbyl, or substituted heteroatom-containing hydrocarbyl. When A is hydroxyl, the nucleoside is a ribonucleoside, and when A is hydrogen, the nucleoside is a deoxyribonucleoside. Preferred L groups are as described in Section II.

B is a nucleobase, generally adenine (A), thymine (T), cytosine (C), guanine (G) or uracil (U), and may be a protected form thereof, e.g., wherein the base is protected with a protecting group such as acetyl, difluoroacetyl, trifluoroacetyl, isobutyryl or benzoyl, or B may be a purine or pyrimidine analog. Suitable analogs will be known to those skilled in the art and are described in the pertinent texts and literature. Common analogs include, but are not limited to, 1-methyladenine, 2-methyladenine, $N^6$-methyladenine, $N^6$-isopentyl-adenine, $N^6$-benzoyladenine 2-methylthio-$N^6$-isopentyladenine, N,N-dimethyladenine, 8-bromoadenine, isocytosine, 2-thiocytosine, 3-methylcytosine, 5-methylcytosine, 5-ethylcytosine, 1-acetylcytosine, 1-isobutyrylcytosine, isoguanine, 1-methylguanine, 2-methylguanine, 7-methylguanine, 2,2-dimethylguanine, 8-bromo-guanine, 8-chloroguanine, 8-aminoguanine, 8-methylguanine, 8-thioguanine, 2-thiothymidine, 4-thiothymidine, 5-fluorouracil, 5-bromouracil, 5-chlorouracil, 5-iodouracil, 5-ethyluracil, 5-propyluracil, 5-methoxyuracil, 5-hydroxymethyluracil, 5-(carboxyhydroxymethyl)-uracil, 5-(methylaminomethyl)uracil, 5-(carboxymethylaminomethyl)-uracil, 5-(1-propynyl)uracil, 2-thiouracil, 4-thiouracil, 5-methyl-2-thiouracil, 5-(2-bromovinyl)uracil, uracil-5-oxyacetic acid, uracil-5-oxyacetic acid methyl ester, pseudouracil, 1-methylpseudouracil, queosine, inosine, 1-methylinosine, hypoxanthine, xanthine, 7-dearaxanthine, 2-aminopurine, 6-hydroxyaminopurine, 6-thiopurine and 2,6-diaminopurine.

One of $R^{11}$ and $R^{12}$ is a blocking group and the other is

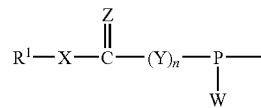

(IV)

in which $R^1$ is hydrogen, a protecting group removable by an elimination reaction, hydrocarbyl, substituted hydrocarbyl, heteroatom-containing hydrocarbyl or substituted heteroatom-containing hydrocarbyl, X and Z are as defined for compounds of formula (I), the subscript "n" is zero or 1, meaning that the linkage Y may or may not be present. If present, Y is $-(Y')_m-(CR^8R^9)-$ wherein m is zero or 1, Y' is hydrocarbylene, substituted hydrocarbylene, heteroatom-containing hydrocarbylene, or substituted heteroatom-containing hydrocarbylene, wherein $R^8$ and $R^9$ are independently selected from the group consisting of hydrogen, hydrocarbyl, substituted hydrocarbyl, heteroatom-containing hydrocarbyl and substituted heteroatom-containing hydrocarbyl. Optimally, either n is zero or n is 1 and m is zero. In the latter case, if $R^8$ and $R^9$ are hydrogen, then in these phosphitylating agents $R^1$ is either hydrogen or a protecting group removable by an elimination reaction. W is $NR^2R^3$, $NR^5R^6$ or DL, wherein $R^2$, $R^3$, $R^4$, $R^5$, $R^6$, D and L are also as defined previously with respect to compounds of formula (I).

Examples of blocking groups suitable as $R^{11}$ or $R^{12}$ include, but are not limited to, heteratom-protecting groups removable by an elimination reaction, generally although not necessarily selected from the group consisting of trityl, monomethoxytrityl ("MMT"), dimethoxytrityl ("DMT"), 9-(9-phenyl)xanthenyl (pixyl), 9-(9-p-methoxyphenyl)xanthenyl ("Mox"), acetyl, pivaloyl, 4-methoxytetrahydropyran-4-yl, tetrahydropyranyl, phenoxyacetyl, isobutyloxycarbonyl, benzyl, trialkylsilyl having from 3 to 9 carbon atoms, 9-fluorenylmethyl carbamate ("Fmoc"), 1-bis-(4-methoxyphenyl)-1'-pyrenylmethyl, and 3-(imidazol-1-ylmethyl)-bis-(4',4"-dimethoxyphenyl)methyl. Greene and Wuts, *Protective Groups in Organic Synthesis*, supra, provides detailed information on the selection of suitable removable blocking groups (i.e., protecting groups) for use as $R^{11}$ or $R^{12}$. The blocking groups do not necessarily, however, have to be removable.

In a particularly preferred embodiment, the nucleoside phosphinoamidite carboxylate has the structure of formula (III) as above wherein one of $R^{11}$ and $R^{12}$ is a blocking group and the other is

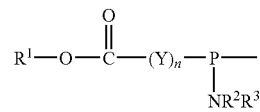

(V)

wherein: $R^1$ is hydrogen, lower alkyl, or a hydroxyl-protecting group removable by an elimination reaction; $R^2$ and $R^3$ are lower alkyl or are linked to form a piperidino, piperazino or morpholino ring; n is zero or 1; and Y is —(Y')$_m$—(CH$_2$)— wherein m is zero or 1 and Y' is lower alkylene.

These nucleoside phosphinoamidite carboxylates may be reacted with water in the presence of an acid catalyst such as tetrazole, or with a weak acid, to undergo conversion to the corresponding H-phosphonites, i.e., nucleoside compounds having the structure of formula (III) wherein one of $R^{11}$ and $R^{12}$ is a blocking group, but the other has the structure of formula (VI)

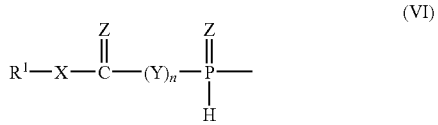

(VI)

wherein $R^1$, X, Y, Z and n are as defined above for nucleosides substituted with a group having the structure of formula IV.

A particularly preferred nucleoside H-phosphonite has the structure of formula (III) wherein, as above, one of $R^{11}$ and $R^{12}$ is a blocking group, but the other has the structure of formula (VII)

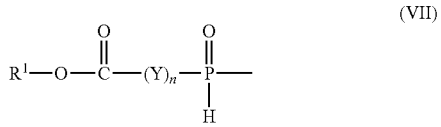

(VII)

wherein: $R^1$ is hydrogen, lower alkyl, or a hydroxyl-protecting group removable by an elimination reaction; n is zero or 1; and Y is —(Y')$_m$—(CH$_2$)— wherein m is zero or 1 and Y' is lower alkylene.

IV. Oligonucleotides

In another embodiment of the invention, modified oligonucleotides are provided that contain at least one internucleotide linkage having the structure of formula (VIII) or (X)

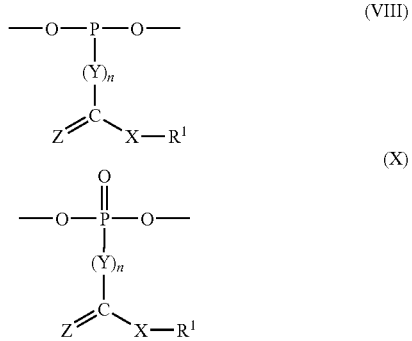

(VIII)

(X)

in which $R^1$, X, Y, Z and n are as defined above for the nucleosides of formula (III), wherein when the internucleotide linkage is (VIII), the oligonucleotide is a "phosphinocarboxylate" oligonucleotide or analog thereof, while when the internucleotide linkage is (X), the oligonucleotide is a "phosphonocarboxylate" oligonucleotide or analog thereof. Oligonucleotides having the phosphinocarboxylate linkage (VIII) may be generally represented as

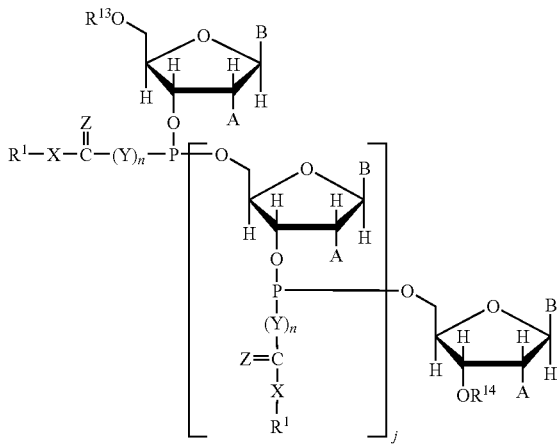

(XI)

wherein $R^1$, X, Y, Z, and n are as defined previously for structures (III) and (IV), A and B are as defined previously for structure (III), and $R^{13}$ and $R^{14}$ are independently hydrogen, a phosphoryl group, a blocking group, or a linkage to a sold support. These phosphinocarboxylate oligonucleotides are generally synthesized on a solid support. For 3'-to-5' synthesis, a support-bound nucleoside monomer is provided having the structure (XII)

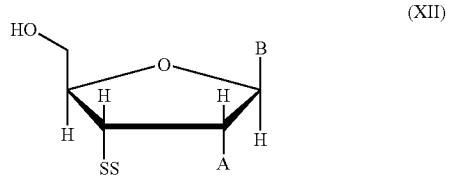

(XII)

wherein A and B are as defined above, and SS represents a solid support or a support-bound oligonucleotide chain. Suitable solid supports are typically polymeric, and may have a variety of forms and compositions and derive from naturally occurring materials, naturally occurring materials that have been synthetically modified, or synthetic materials. The supports may be comprised of organic polymers, inorganic polymers, metals, metal oxides, or combinations thereof. Suitable substrate materials include, but are not limited to, supports that are typically used for solid phase chemical synthesis, such as: polymeric materials (e.g., polystyrene, polyvinyl acetate, polyvinyl alcohol, polyvinyl chloride, polyvinyl pyrrolidone, polyacrylonitrile, polyacrylamide, polymethyl methacrylate, polytetrafluoroethylene, polyethylene, polypropylene, polyvinylidene fluoride, polycarbonate, polytetrafluoroethylene, divinylbenzene styrene-based polymers, and copolymers of hydroxyethyl methacrylate and methyl methacrylate), including grafted polymers and soluble polymers; cellulosic polymers and other polysaccharides, including agarose (e.g., Sepharose®) and dextran (e.g., Sephadex®); silica and silica-based materials (e.g., silica, quartz, aluminosilicates and borosilicates); glasses (particularly controlled pore glass, or "CPG") and functionalized glasses; ceramics, including metal oxides; metals; and such substrates treated with surface coatings, e.g., with microporous polymers (particularly cellulosic polymers such as nitrocellulose).

The initial monomer will typically be covalently attached to the support surface, typically although not necessarily through a linking group as is known in the art. A linking group, if present, should have a length sufficient to allow a complementary oligonucleotide to bind to the complete support-bound oligonucleotide. The linking group may contain a cleavable site to allow release of the completed oligonucleotide from the substrate surface after use, i.e., after completion of a hybridization assay. Cleavable sites may be restriction sites (i.e., sites cleavable by restriction endonucleases), or they may be chemically or photolytically cleavable sites, as will be appreciated by those of ordinary skill in the art.

The monomer to be added has the structure of formula (XIII)

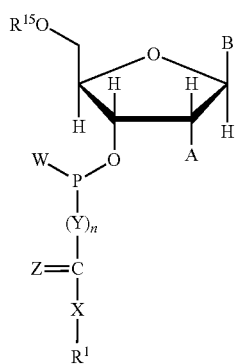

(XIII)

wherein $R^{15}$ is a hydroxyl-protecting group and the remaining substituents are as defined above. Examples of methods and reagents for protection of 5'-hydroxyl groups are well known and described in a number of references, including Happ et. al. (1988) *Nucleosides & Nucleotides* 7:813; Chattopadhyaya et. al., (1980) *Nucl. Acids Res.* 8:2039]; Seliger et. al. (1985) *Nucleosides Nucleotides* 4:153; Ma et. al. (1987) *Nucleosides & Nucleotides* 6:491; Pfleiderer et. al. (1986) *Chem Scr.* 26:147; McGall et. al. (1997) *J. Am. Chem. Soc.* 119:5081; and Scaringe et. al. (1998) *J. Am. Chem. Soc.* 120:11820. The coupling reaction is conducted under standard conditions used for the synthesis of oligonucleotides and conventionally employed with automated oligonucleotide synthesizers. Such methodology will be known to those skilled in the art and is described in the pertinent texts and literature, e.g., in D. M. Matteuci et al. (1980) *Tetrahedron Lett.* 521:719 and U.S. Pat. No. 4,500,707. The product of the coupling reaction has the structure (XIV)

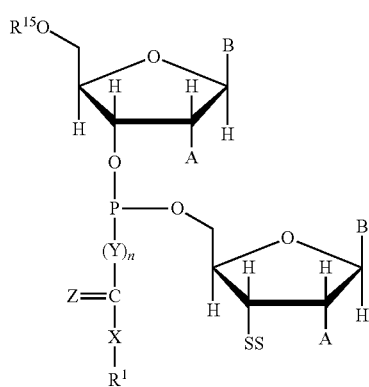

(XIV)

Following coupling, unreacted hydroxyl groups are optionally capped with a suitable capping agent. Then, if desired, the phosphinocarboxylate linkage can be oxidized with a suitable oxidizing agent to provide the corresponding phosphonocarboxylate linkage, shown in the following structure:

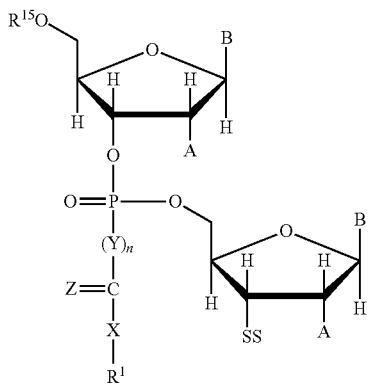

(XV)

Next, the protecting group $R^{15}$ is removed, and an additional 5'-protected phosphinocarboxylate monomer is added in a similar manner. The process is repeated until the oligonucleotide is of the desired length. Following synthesis, the oligonucleotide may, if desired, be cleaved from the solid support.

The method of the invention also lends itself to synthesis in the 5'-to-3' direction. In such a case, the initial step of the synthetic process involves attachment of a nucleoside monomer to a solid support at the 5' position, leaving the 3' position available for covalent binding of a subsequent monomer. In this embodiment, i.e., for 5'-to-3' synthesis, a support-bound nucleoside monomer is provided having the structure (XV)

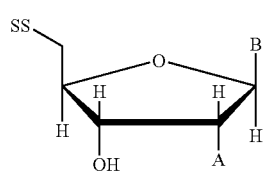

(XV)

wherein A, B, and SS are as defined above for structure (XII). The protected monomer to be added has the structure of formula (XVI)

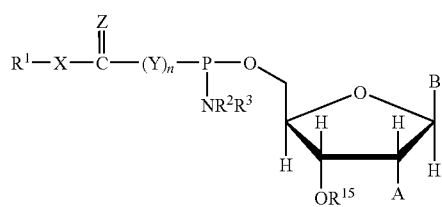

(XVI)

giving rise to the coupled product (XVII)

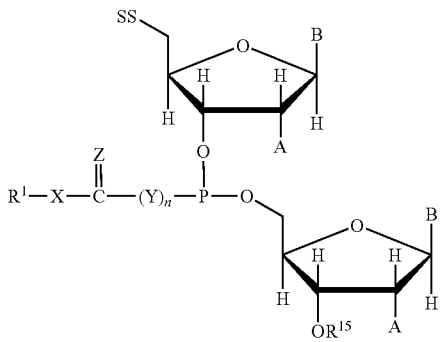

(XVII)

Oxidation of the phosphinocarboxylate to the phosphonocarboxylate, deprotection and successive addition of additional nucleosides may be carried out as above, followed by cleavage of the final oligonucleotide product from the solid support, if desired. With respect to $R^{15}$, exemplary methods and reagents for orthogonal protection of 3'-hydroxyl groups are given by Koga et. al. (1991) *J. Org. Chem.* 56:3757 and Pirrung et. al., U.S. Pat. No. 5,908,926, issued Jun. 1, 1999.

These phosphinocarboxylate and phosphonocarboxylate oligonucleotides find applications in a variety of areas, for example: as therapeutic agents, particularly as therapeutic agents in antisense-, ribozyme- and aptamer-based strategies; as diagnostic agents in target validation, to test selected proteins for suitability as a therapeutic target; in investigating the mechanism and stereochemistry of biochemical reactions; and in the mapping of nucleic acid protein interactions. Furthermore, since the novel oligonucleotides have been found to direct the hydrolysis of complementary RNA in the presence of RNaseH, they are also useful as agents for eliciting RNaseH activity. Finally, because the oligonucleotides have reduced charge relative to relative to oligonucleotides with standard phosphonate linkages, they readily pass through body membranes and in addition have enhanced utility in the area of mass spectrometry.

It may also be desirable to prepare substrate-bound arrays of phosphinocarboxylate and phosphonocarboxylate oligonucleotides as provided herein. High density oligonucleotide arrays are now well known and in commercial use for a number of purposes. For example, these so-called "DNA chips" or "gene chips" can be used in gene expression analysis and mutation detection, polymorphism analysis, mapping, evolutionary studies, and other applications. The term "array" as used herein refers to a regular, ordered, two-dimensional arrangement of oligonucleotides covalently bound or otherwise attached to a substrate surface. Substrate-bound arrays comprised of one or more phosphinocarboxylate or phosphonocarboxylate oligonucleotides of the invention may be prepared using now-conventional techniques, e.g., by "spotting" pre-synthesized oligonucleotides onto designated sites of a substrate surface, or by synthesizing the oligonucleotides in situ, on a solid support. Specific methods for forming and using oligonucleotide arrays will be known to those skilled in the art and/or are described in the pertinent texts and literature.

It is to be understood that while the invention has been described in conjunction with the preferred specific embodiments thereof, that the description above as well as the example which follows are intended to illustrate and not limit the scope of the invention. Other aspects, advantages and modifications within the scope of the invention will be apparent to those skilled in the art to which the invention pertains.

All patents, patent applications, journal articles and other references mentioned herein are incorporated by reference in their entireties.

EXPERIMENTAL

The practice of the present invention will employ, unless otherwise indicated, conventional techniques of synthetic organic chemistry, biochemistry, molecular biology, and the like, which are within the skill of the art. Such techniques are explained fully in the literature.

The following examples are put forth so as to provide those of ordinary skill in the art with a complete disclosure and description of how to prepare and use the compounds disclosed and claimed herein. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric. Unless otherwise indicated, all starting materials and reagents were obtained commercially and used without further purification.

Also, in these examples and throughout this specification and figures, the abbreviations employed have their generally accepted meanings, as follows:

| | |
|---|---|
| ACN | acetonitrile |
| CPG | control pore glass |
| CSO | (1S)-(+)(10-camphorsufonyl)-oxaziridine |
| DBU | 1,8-diazabicyclo[5.4.0]undec-7-ene |
| DMAP | 4-dimethylaminopyridine |
| DMT | dimethoxytrityl |
| DTT | dithiothreitol |
| EDTA | ethylenediaminetetraacetic acid |
| HEPES | 4-(2-hydroxyethyl)-1-piperazine-ethanesulfonic acid |
| iPr | isopropyl |
| ODN | oligodeoxyribonucleotide |
| Py | pyridine |
| TCA | trichloroacetic acid |
| THF | tetrahydrofuran |
| SVP | snake venom phosphodiesterase |

Example 1

Preparation of bis-(N,N-diisopropylamino)chlorophosphine

A 5-liter, 3-neck, round-bottom flask was equipped with a Fredrich's condenser, a ground glass stirrer bearing, a silicon rubber septum, and placed under dry argon. Two liters (1,600 grams, 15.9 mmols, 7.0 eq) of anhydrous diisopropyl amine was added to the flask. The diisopropyl amine was diluted by the addition of two liters of anhydrous acetonitrile. The solution was mixed with a mechanical stirrer attached to a glass stir rod and Teflon blade. An ice/water bath was placed under the 5-liter flask, and the amine solution allowed to cool for 30 min. Phosphorus trichloride (313 grams, 2.3 mmols, 1.0 eq) was dissolved in 1 liter of anhydrous acetonitrile in a separate dry 1-liter flask. The mechanical stirrer was set to vigorous stirring and the phosphorus trichloride solution added slowly to the stirring flask by cannula. Once the addition was complete, the ice/water bath was removed, and the reaction was allowed to warm to room temperature. The reaction was stirred overnight and the extent of the reaction determined by $^{31}$P NMR of en aliquot of the reaction mixture using an external lock. Complete conversion of the starting material, phosphorus trichloride (δ 201 ppm), into the product at δ 134 ppm, demonstrated completion of the desired reaction. The reaction mixture was filtered to remove the bulk of the diisopropylamine hydrochloride, which had precipitated. The precipitate was washed with anhydrous ether and the filtrates evaporated into a 2-liter round-bottom flask. The resulting evaporated product was a semi-crystalline solid, which was suspended in 1 liter of anhydrous hexanes. The flask was heated on a mantel, to allow the hexanes to boil. The hot liquid was filtered through a Schlenk filter-funnel to remove residual amine hydrochloride. This resulting clear yellow liquid was evaporated to one half the original volume and placed in a freezer to allow the product to recrystallize. The recrystallized product was isolated by filtration and dried in a vacuum desiccator, yielding 447 grams (74% yield).

Example 2

Synthesis of N,N-diisopropylamino dichlorophosphine

Bis-(N,N-Diisopropylamino)chlorophosphine, 10 grams (37 mmols), was dissolved in 500 ml of anhydrous acetonitrile. Phosphorus trichloride, 5.16 grams (37 mmols), was added to the solution and the reaction was allowed to stir over-night at room temperature. The reaction was assayed for completion by $^{31}$P NMR of an aliquot of the reaction using an external lock. Complete conversion of the starting material at δ 134 ppm to the product at δ 165 ppm was observed. The solvent was evaporated from the reaction mixture on a rotary evaporator and the resulting oil distilled under vacuum yielding 5.7 grams of product (81% yield).

Example 3

Synthesis of Acetic Acid, (bis-N,N-(diethylamino)phosohino)-methyl ester

A 500 ml 3-neck round bottom flask was equipped with a reflux condenser, magnetic stir bar and two addition funnels. 13.1 grams, 200 mmol of granular zinc was placed in the bottom of the flask. Bis-(N,N-diethylamino)chlorophosphine (21.1 grams, 100 mmol) and methyl bromoacetate (14.1 grams, 100 mmol) were each dissolved in 200 ml of anhydrous ether. The two ether solutions were placed in the dropping funnels and the reflux condenser fitted with a dry argon line. 30 ml of each solution was ran into the round bottom flask and the mixture stirred vigorously. The reaction mixture was heated with a heat gun until the ether boiled. The heat was kept on the mixture until the reaction mixture became clear and slightly yellow. At this point, the reaction continued to boil without addition of heat due to the exothermic nature of the reaction. Steady addition of the two ether solutions kept the reaction at a vigorous boil. After the addition was complete, the reaction was kept at a boil by the addition of heat for 10 min. The reaction was allowed to cool and an aliquot was removed for $^{31}$P NMR. The $^{31}$P NMR demonstrated complete conversion of the starting material δ 159.2 ppm to the product at δ 50.9 ppm. The reaction mixture was decanted leaving behind the unreacted zinc and the ether was removed under vacuum on a rotary evaporator. The product was isolated by triturating with pentanes. The product was characterized by $^1$H NMR singlet δ 3.66 (integration 3), doublet δ 2.93, 2.91 (integration 2), quartet δ 2.72 (integration 8), triplet δ 1.26 (integration 12). Electron Impact Mass Spectrometry gave a molecular radical of 248 m/e with fragmentation loss of CH$_2$COOCH$_3$ at 175 m/e. This correctly identified product gave different $^{31}$P NMR characterization than the product reported by Novikova et. at. (1976), *Zhurnal Obshchei Khimii* 46:575. However, upon attempted distillation, the acetic acid (bis-N,N-(diethylamino)phosphino)-methyl ester decomposed into a complex reaction mixture. The decomposed, unidentified, products contained a $^{31}$P NMR peak at the mis-reported chemical shift of δ 82 ppm (-82 ppm).

Example 4

Synthesis of Acetic Acid, (bis-N,N-(diisopropylamino)phosphino)-methyl ester

In a 1000 ml three neck round bottom flask, granular zinc metal 7.2 grams, 110 mmol was placed in the bottom with a magnetic stir-bar. The three neck flask was fitted with a Fredrich's condenser and two 500 ml addition funnels. The addition funnels were filled with minimum-volume ether solutions of bis-N,N-diisopropylaminochlorophosphine (20 grams, 75 mmol, 1.0 eq), and methylbromoacetate (11.6 grams, 82.5 mmol, 1.1 eq). Approximately one third of each solution was added to the flask and the mixture was heated with a heat gun until the Reformatsky reaction was initiated. Once initiated, the reaction was continued by constant addition of the two solutions. Once the addition was complete, the reaction was stirred for 15 min. The extent of the reaction was determined by $^{31}$P NMR. The starting material gave a chemical shift of δ 135 ppm and the product a chemical shift of δ 49 ppm. The reaction was fitted with a mantel and the ether was refluxed until the starting material was consumed as monitored by $^{31}$P NMR. The reaction was evaporated and the resulting oil was extracted with anhydrous hexanes. The hexanes fraction was evaporated and the product distilled under vacuum to give a colorless oil, 11.8 grams, 54% yield. The product was characterized by $^1$H NMR singlet δ 3.68 (integration 3), multiplet δ 3.55 (integration 4), doublet δ 2.93, 2.91 (integration 2), multiplet δ 1.30 (integration 24). Electron Impact Mass Spectrometry gave a molecular radical of 304 m/e with fragmentation loss of CH$_2$COOCH$_3$ at 231 m/e.

Example 5

Synthesis of Acetic Acid, (bis-N,N-(diisopropylamino)phosphino)-dimethylcyano-ethyl ester Dimethylcyanoethylbromoacetate was synthesized from bromoacetyl bromide and 3-hydroxy-3methylbutyronitrile. The bromoacetyl bromide (108 grams, 600 mmol) was dissolved in 500 ml of anhydrous toluene in a 1 liter round bottom flask. The 3-hydroxy-3methylbutrionitrile (50 grams, 500 mmol) was added slowly with stirring. The round bottom flask was fitted with a Friedrich's condenser and a drying tube. The outlet on the drying tube was fitted with a thick hose and the exhaust taken to an acid trap. The reaction was heated to reflux using a mantel and the reaction was refluxed to effluvium HBr. The reaction was refluxed overnight then cooled to room temperature and evaporated to an oil on a rotary evaporator. The oil was distilled under vacuum. The first fraction was of wide boiling range and was discarded. The second, major, fraction was of constant boiling range and gave 97.3 grams of a, clear, colorless liquid. $^1$H NMR of this material gave three singlets: δ 3.75 (relative integration 2), δ 2.86 (relative integration 2), δ 1.53 (relative integration 6). Bis-N,N-diisopropylamino-chlorophosphine (20 grams, 75 mmol, 1.0 eq) was dissolved in 160 ml of anhydrous THF in a 500 ml round bottom flask. The flask was stoppered and allowed to stir until all the phosphine was dissolved. Once dissolved, 100 ml of anhydrous ether was added to the phosphine solution. Dimethylcyanoethylbromoacetate (MW 220), 18.2 grams, 82.5 mmol, 1.1 eq was dissolved in 75 ml of anhydrous ether. Granular zinc metal, 7.2 grams, 110 mmol was placed in the bottom of a three neck round bottom flask along with a magnetic stir-bar. The round bottom flask was fitted with a Friedrich's condenser and two addition funnels. The phosphine solution was placed in one of the addition funnels and the bromoacetate was placed in the other. 85 ml of the phosphine solution and 25 ml of the bromoacetate solution were added to the zinc metal. The reaction was heated with a heat gun until the ether vigorously refluxed. The heat was removed and the reflux allowed to quite. Heat was again applied and the process was repeated until an exothermic reaction was noticeable. The slightly cloudy, colorless reaction became clear and slightly yellow once the exothermic reaction began. The reaction was continued by addition of the two solutions and the reaction was kept at reflux by use of the heat gun. The reaction was kept at reflux for 30 min and then allowed to cool. The reaction was monitored for completeness by $^{31}$P NMR. The starting material at δ 135 ppm was converted to a single product at δ 48 ppm. The cooled reaction mixture was transferred to a 1-liter round bottom flask and the THF and ether removed on a rotary evaporator. The resulting viscous oil was extracted three times with anhydrous hexanes. The extraction converted the viscous oil to a solid and the solid was dissolved in anhydrous acetonitrile. The acetonitrile solution was extracted twice with anhydrous hexanes and all the hexanes fractions combined and evaporated under vacuum to a slightly yellow oil. The acetonitrile solution was analyzed by $^{31}$H NMR for absence of the product at δ 48 ppm, and discarded. The isolated product was further purified by dissolving in anhydrous hexanes and placing in a freezer overnight. The resulting hexanes solution was decanted into a clean, dry, 500 ml round bottom flask. The hexanes were removed by evaporation to give 16.4 grams of purified product, 88% yield. The product was characterized by $^1$H NMR: multiplet δ 3.48 (integration 4), singlet δ 2.99 (integration 2), doublet δ 2.80, 2.78 (integration 2), multiplet δ 1.30 (integration 24). Electron Impact Mass Spectrometry gave a molecular radical of 371 m/e with fragmentation loss of $CH_2COOC(CH_3)_2CH_2CN$ at 231 m/e.

Example 6

Synthesis of Formic acid, (bis-N,N-(diisopropylamino)phoshino)-methyl ester

Methyl chloroformate (79.7 grams, 843 mmol, 3.0 eq) was dissolved in 250 ml of anhydrous tetrahydrofuran (THF) in a dry 500 ml round bottom flask containing activated 3A molecular sieves and stored overnight to remove traces of HCl. Bis-N,N-diisopropylaminochlorophosphine (75.0 grams, 281 mmol, 1.0 eq) was dissolved in 200 ml anhydrous THF in a dry 250 ml round bottom flask. In a separate 500 ml round bottom flask, 200 ml of anhydrous THF was added with a magnetic stir bar. Lithium aluminum hydride (LiAlH$_4$, 10.7 grams, 281 mmol, 1.0 eq) was added slowly with stirring. The LiAlH$_4$ solution was fitted with an argon line and cooled in an ice/water bath. The phosphine solution was slowly cannulated into the stifling LiAlH$_4$ solution over 10 min. After addition was complete, the ice/water bath was removed and the reduced phosphine solution was allowed to warm to room temperature. The reaction was checked by $^{31}$P NMR. The reaction was complete when the starting material (singlet, 135.2 ppm) was converted completely to the product (singlet, 38.8 ppm). The reaction mixture was filtered through a sintered glass Schlenk funnel into a dry 500 ml round bottom flask containing a magnetic stir-bar and 20 grams of sodium metal spheres under argon. The round bottom flask was fitted with a Friedrich's condenser and the solution refluxed under argon for 3 hours using a mantel. The mantel was removed and the resulting solution allowed to cool to room temperature. The methyl chloroformate solution was transferred by cannula to a dry 1000 ml round bottom flask containing a magnetic stir-bar. The methyl chloroformate solution was fitted with an argon line and cooled in an ice/water bath. The phosphine solution was cannulated into the stirring solution of the methyl chloroformate. After the addition was complete, the reaction was monitored by $^{31}$P NMR. The reaction was complete when the starting material (singlet, 43.2 ppm) was converted to the product (singlet, 52.0 ppm) as determined by $^{31}$P NMR. The reaction was quenched by the dropwise addition of triethyl amine, 85.2 grams, 843 mmol, 3.0 eq. The entire mixture was evaporated on a rotary evaporator and the residual oil triturated several times with anhydrous hexanes. The hexanes were evaporated and resulting oil distilled under high vacuum. The product gave a clear, colorless, liquid which distilled at 95° C. at 0.04 mm Hg. The purified product was dissolved in deuterated acetonitrile and characterized by $^1$H NMR; singlet δ 3.69 (integration 3), multiplet δ 3.55 (integration 4), multiplet δ 1.30 (integration 24). Electron Impact Mass Spectrometry gave a molecular radical of 290 m/e with fragmentation loss of $COOCH_3$ at 231 m/e.

Example 7

Synthesis of Formic acid, (bis-N,N-(diisopropylamino)phosphino)-cyanoethyl ester Cyanoethyl chloroformate was synthesized from phosgene and 3-hydroxyproprionitrile. The phosgene was obtained as a 20% solution in toluene. The toluene solution (500 ml, 100 grams, 1.0 mol) was placed in a 1-liter round bottom flask with a magnetic stir-bar. The 3-hydroxyproprionitrile (23.4 grams, 0.33 mol) was dissolved in anhydrous tetrahydrofuran (THF) and placed in an addition funnel. The THF solution was added dropwise to the phosgene solution and the reaction mixture allowed to stir at room temperature overnight. The reaction mixture was evaporated to an oil using a rotary evaporator placed in a fume hood. The vacuum was applied using a Teflon-head diaphragm pump and the exhaust bubbled through a sodium bicarbonate solution to trap and neutralize the excess phosgene. The toluene removed from the reaction was poured into methanol and further neutralized with water before disposal. The resulting product was isolated and purified by distillation under vacuum. The $^1$H NMR of the distilled material in CDCl$_3$ gave 2 triplets centered at δ 2.77 ppm (relative integration 2.0), and δ 4.44 ppm (relative integration 2.0). The $^{13}$C NMR of the distilled material in CDCl$_3$ gave 4 decoupled singlets at δ 148.95, δ 114.62, δ 63.94, and δ 16.18. In a 500 ml round bottom flask 200 ml of anhydrous THE was added with a magnetic stir bar. Lithium aluminum hydride (10.7 grams, 281 mmol, 1.0 eq) was added slowly with stirring. The LiAlH$_4$ solution was fitted with an argon line and cooled in an ice/water bath. Bis-N,N-diisopropylaminochlorophosphine (75.0 grams, 281 mmol, 1.0 eq) was dissolved in a minimum volume of anhydrous THF. The phosphine solution was slowly cannulated into the stirring LiAlH$_4$ solution over 10 min. After addition was complete, the ice/water bath was removed and the reduced phosphine solution was allowed to warm to room temperature. The reaction was checked by $^{31}$P NMR. The reaction was complete when the starting material (singlet, δ 135.2 ppm) was converted completely to the product (singlet, δ 42.8 ppm). The reaction mixture was filtered through a sintered glass Schlenk funnel into a dry 500 ml round bottom flask containing a magnetic stir-bar and 20 grams of sodium metal spheres under argon. The round bottom flask was fitted with a Friedrich's condenser and the solution refluxed under argon for 3 hours using a mantel. The mantel was removed and the resulting solution allowed to cool to room temperature. The cyanoethylchloroformate (843 mmol, 112.5 grams) was dissolved in anhydrous THF, 600 ml in a 2-liter flask, and cooled in an ice/water bath. The reduced phosphine was added to the chloroformate by cannula and allowed to stir for one hour. The ice bath was removed and the reaction was allowed to warm to room temperature. The reaction was checked for completion by $^{31}$P NMR. The product gave a single peak at δ 52.0 ppm. The reaction was continued until the starting material was completely converted to the product. The reaction mixture was then cannulated into separate, dry, 2-liter round bottom flask containing 500 ml of anhydrous triethylamine. The resulting precipitate was removed by filtration. The filtrate was evaporated to a thick oil and the oil was extracted with anhydrous hexanes. The hexanes were evaporated and the product purified by vacuum distillation. The product was obtained as a colorless oil (65.6 grams), 71% yield. The purified product gave a $^{31}$P NMR peak at δ 53.0 ppm. The purified product was dissolved in deuterated acetonitrile and characterized by $^1$H NMR; doublet δ 1.34, 1.30 (integration 24), triplet δ 2.86 (integration 2), multiplet δ 3.52 (integration 4), triplet δ 4.37 (integration 2). Electron Impact Mass Spectrometry gave a molecular radical of 329 m/e with fragmentation with loss of COOCH$_2$CH$_2$CN at 231 m/e.

Example 8

Synthesis of Acetic Acid, (N,N-(diisopropylamino) cyanoethoxyphosphino)-dimethylcyanoethyl ester Acetic acid, (bis-N,N-(diisopropylamino)phosphino)-dimethylcyanoethyl ester, 5 grams, 13.5 mmol, was dissolved in 150 ml of anhydrous dichloromethane in a 250 ml round bottom flask. 3-Hydroxyproprionitrile, 1 gram, 14.8 mmol, was added to the phosphine mixture and the solution stirred using a magnetic stir-bar. Tetrazole (0.75 grams, 10.8 mmol) was added to the mixture and the reaction allowed to stir overnight. The mixture was assayed for completion by TLC in 50/50, hexanes/ethyl acetate. The product was isolated by silica gel, flash chromatography using an ethyl acetate gradient in hexanes. The product was evaporated to an oil yielding 4.3 grams, 12.6 mmol (94% yield) and analyzed by $^{31}$P NMR δ 124.1 ppm, and EI Mass spectrometry giving an exact mass of 341.19 (341.39 calculated).

Example 9

General Method for Synthesis of Protected Nucleoside Carboxylic Acid Phosphinoamidites The synthesis of protected nucleoside carboxylic acid phosphinoamidites was accomplished by the general procedure as follows. The protected nucleosides were dissolved in anhydrous dichloromethane at a concentration of 0.05 to 0.1M depending upon their solubility. The corresponding carboxylic acid bis-aminophosphonite ester, 1.2 molar equivalents, was added to the dichloromethane solution with stirring. After complete dissolution of the phosphonite, 0.8 molar equivalents of tetrazole was added to the reaction mixture. The tetrazole was added by pipette from a 0.45 M solution of tetrazole in anhydrous acetonitrile. The reaction was allowed to stir for 24 hr. and was then analyzed for extent of reaction by $^{31}$P NMR and silica gel TLC (eluted with ethyl acetate). The reaction was determined to be complete by spot-to-spot conversion of the protected nucleoside starting material to faster eluting spots on TLC or by loss of the bis-aminophosphonite ester starting material by $^{31}$P NMR. The reaction was quenched by addition of an equal volume of concentrated sodium bicarbonate. The mixture was stirred to produce an emulsion then transferred to a separatory funnel. The emulsion was allowed to separate, and the dichloromethane layer removed to an Erlenmeyer flask containing anhydrous sodium sulfate. The solution was allowed to dry over the sodium sulfate for 1 hour then decanted to a round bottom flask. The sodium sulfate was rinsed with anhydrous dichloromethane and the rinsing added to the round bottom flask. The dichloromethane was removed by evaporation on a rotary evaporator and the resulting viscous oil purified by column chromatography on silica gel. The column was equilibrated with hexanes/ethyl acetate (50/50, vol./vol.). The viscous oil was redissolved in a minimum volume of ethyl acetate, which was then diluted with hexanes up to a 50/50 solution, if allowed by solubility. The hexanes/ethyl acetate solution was added to the top of the column and the products were eluted with a step-gradient of 50/50 hexanes/ethyl acetate (vol./vol) to 100% ethyl acetate. Fractions containing UV-active material were collected and analyzed by silica gel TLC (eluted with ethyl acetate). Those fractions, which contained the product were collated and evaporated to a foam on a rotary evaporator. The resulting foam product was dried overnight in vacuo and analyzed by $^{31}$P NMR, and FAB mass spectroscopy.

Example 10

Synthesis of 3'-O-(diisopropylamino)-phosphinoformic acid methyl ester-5'-O-dip-anisylphenylmethyl thymidine 5'-DMT thymidine (10 grams, 18.4 mmoles) was reacted with formic acid, (bis(diisopropylamino)phosphino)-methyl ester (5.4 grams, 18.4 moles) in the presence of tetrazole (1.03 grams, 14.7 mmoles) for 48 hrs. The product was purified on silica gel by eluting the column with 50/50 hexanes/ethyl acetate giving 9.17 grams (68% yield). Fractions from the column were collected and evaporated to a foam. The resulting purified phosphinoamidite was analyzed by $^{31}$P NMR, giving a set of diastereomers at δ107.43 and δ108.23 ppm, and FAB Mass Spectroscopy FAB+ 734 m/e (m+1), FAB– 732 m/e (m–1).

Example 11

Synthesis of 3'-O-(diisopropylamino)-phosphinoformic acid β-cyanoethyl ester-5'-O-di-p-anisylphenylmethyl thymidine 5'-DMT thymidine (10 grams, 18.4 mmoles) was reacted with formic acid, (bis(diisopropylamino)phosphino)-cyanoethyl ester (6.1 grams, 18.4 mmoles), in the presence of tetrazole (1.03 grams, 14.7 mmoles) for 48 hrs. The product was purified on silica gel by eluting the column with 50/50 hexanes/ethyl acetate and the resulting purified product gave 9.97 grams (74% yield). Fractions from the column were collected and evaporated to a foam. The resulting purified phosphinoamidite was analyzed by $^{31}$P NMR, giving a set of diastereomers at δ 108.38 and δ108.42 ppm, and FAB Mass Spectroscopy FAB+ 733 m/e (m+1), FAB– 731 m/e (m–1).

Example 12

Synthesis of 3'-O-(diisopropylamino)-phosphinoformic acid methyl ester-5'-O-di-p-anisylphenylmethyl-N-4-benzoylcytosine 5'-DMT-N-4-benzoylcytosine (10 grams, 15.8 mmoles) was reacted with formic acid, (bis(diisopropylamino)phosphino)-methyl ester (4.6 grams, 15.8 mmoles), in the presence of tetrazole (0.89 grams, 12.6 mmoles) for 48 hrs. The product was purified on silica gel by eluting the column with 75/25 hexanes/ethyl acetate and the resulting purified product gave 8.96 grams (69% yield). Fractions from the column were collected and evaporated to a foam. The resulting purified phosphinoamidite was analyzed by $^{31}$P NMR, giving a set of diastereomers at δ 107.75 and δ 109.32 ppm, and FAB Mass Spectroscopy FAB+ 823 m/e (m+1), FAB– 821 m/e (m–1).

Example 13

Synthesis of 3'-O-(diisopropylamino)-phosphinoformic acid β-cyanoethyl ester-5'-O-di-p-anisylphenylmethyl-N-4-benzoylcytosine 5'-DMT-N-4-benzoylcytosine (10 grams, 15.8 mmoles) was reacted with formic acid, (bis(diisopropylamino)phosphino)-cyanoethyl ester (5.2 grams, 15.8 mmoles), in the presence of tetrazole (0.89 grams, 12.6 moles) for 48 hrs. The product was purified on silica gel by eluting the column with 75/25 hexanes/ethyl acetate, and the resulting purified product gave 9.93 grams (73% yield). Fractions from the column were collected and evaporated to a foam. The resulting purified phosphinoamidite was analyzed by $^{31}$P NMR, giving a set of diastereomers at δ 107.66 and δ109.22 ppm, and FAB Mass Spectroscopy FAB+ 862 m/e (m+1), FAB– 860 m/e (m–1).

Example 14

Synthesis of 3'-O-(diisopropylamino)-phosphinoformic acid methyl ester-5'-O-di-p-anisylphenylmethyl-N-4-acetylcytosine 5'-DMT-N-4-acetylcytosine (10 grams, 17.5 mmoles) was reacted with formic acid, (bis(diisopropylamino)phosphino)-methyl ester (5.1 grams, 17.5 mmoles), in the presence of tetrazole (0.98 grams, 14.0 mmoles) for 24 hrs. The product was purified on silica gel by eluting the column with 100% ethyl acetate, and the resulting purified product gave 10.24 grams (77% yield). Fractions from the column were collected and evaporated to a foam. The resulting purified phosphinoamidite was analyzed by $^{31}$P NMR, giving a set of diastereomers at δ 107.91 and δ 109.48 ppm, and FAB Mass Spectroscopy FAB+ 761 m/e (m+1), FAB– 759 m/e (m–1).

Example 15

Synthesis of 3'-O-(diisopropylamino)-phosphinoformic acid β-cyanoethyl ester-5'-O-di-p-anisylphenylmethyl-N-4-acetylcytosine 5'-DMT-N-4-acetylcytosine (10 grams, 17.5 mmoles) was reacted with formic acid, (bis(diisopropylamino)phosphino)-cyanoethyl ester (5.8 grams, 17.5 mmoles), in the presence of tetrazole (0.98 grams, 14.0 mmoles) for 48 hrs. The product was purified on silica gel by eluting the column with 100% ethyl acetate, and the resulting purified product gave 11.33 grams (81% yield). Fractions from the column were collected and evaporated to a foam. The resulting purified phosphinoamidite was analyzed by $^{31}$P NMR, giving a set of diastereomers at δ 108.58 and δ 109.50 ppm, and FAB Mass Spectroscopy FAB+ 800 m/e (m+1), FAB– 798 m/e (m–1).

Example 16

Synthesis of 3'-O-(diisopropylamino)-phosphinoformic acid methyl ester-5'-O-di-p-anisylphenylmethyl-9-N-benzoyl adenosine 5'-DMT-N-9-benzoyl adenosine (10 grams, 15.3 mmoles) was reacted with formic acid, (bis(diisopropylamino)phosphino)-methyl ester (4.43 grams, 15.3 mmoles), in the presence of tetrazole (0.86 grams, 12.24 mmoles) for 24 hrs. The product was purified on silica gel by eluting the column with 50/50 hexanes/ethyl acetate, and the resulting purified product gave 10.23 grams (79% yield). Fractions from the column were collected and evaporated to a foam. The resulting purified phosphinoamidite was analyzed by $^{31}$P NMR, giving a set of diastereomers at δ 107.68 and δ 108.56 ppm, and FAB Mass Spectroscopy FAB+ 847 m/e (m+1), FAB– 845 m/e (m–1).

Example 17

Synthesis of 3'-O-(diisopropylamino)-phosphinoformic acid β-cyanoethyl ester-5'-O-di-p-anisylphenylmethyl-9-N-benzoyl adenosine 5'-DMT-N-9-benzoyl adenosine (10 grams, 15.3 mmoles) was reacted with formic acid, (bis(diisopropylamino)phosphino)-cyanoethyl ester (5.03 grams, 15.3 mmoles), in the presence of tetrazole (0.86 grams, 12.24 mmoles) for 24 hrs. The product was purified on silica gel by eluting the column with 50/50 hexanes/ethyl acetate, and the resulting purified product gave 8.40 grams (62% yield). Fractions from the column were collected and evaporated to a foam. The resulting purified phosphinoamidite was analyzed by $^{31}$P NMR, giving a set of diastereomers at δ 108.56 and δ 108.67 ppm, and FAB Mass Spectroscopy FAB+ 886 m/e (m+1), FAB– 884 m/e (m–1).

Example 18

Synthesis of 3'-O-(diisopropylamino)phosphinoformic acid methyl ester-5'-O-di-ρ-anisylphenylmethyl-N-2-isobutyrylguanosine 5'-DMT-N-2-isobutyrylguanosine (10 grams, 15.7 mmoles) was reacted with formic acid, (bis(diisopropylamino)phosphino)-methyl ester (4.55 grams, 15.7 mmoles), in the presence of tetrazole (0.88 grams, 12.56 mmoles) for 24 hrs. The product was purified on silica gel by eluting the column with 100% ethyl acetate, and the resulting purified product gave 10.66 grams (82% yield). Fractions from the column were collected and evaporated to a foam. The resulting purified phosphinoamidite was analyzed by $^{31}$ρ NMR, giving a set of diastereomers at δ 107.60 and δ 108.35 ppm, and FAB Mass Spectroscopy FAB+ 829 m/e (m+1), FAB– 827 m/e (M-1).

Example 19

Synthesis of 3'-O-(diisopropylamino)-phosphinoformic acid β-cyanoethyl ester-5'-O-di-ρanisylphenylmethyl-N-2-isobutyry guanosine 5'-DMT-N-2-isobutyrylguanosine (10 grams, 15.7 mmoles) was reacted with formic acid, (bis(diisopropylamino)phosphino)-cyanoethyl ester (5.17 grams, 15.7 mmoles), in the presence of tetrazole (0.88 grams, 12.56 mmoles) for 24 hrs. The product was purified on silica gel by eluting the column with 100% ethyl acetate, and the resulting purified product gave 10.89 grams (80% yield). Fractions from the column were collected and evaporated to a foam. The resulting purified phosphinoamidite was analyzed by $^{31}$P NMR, giving a set of diastereomers at 108.36 and δ 108.45 ppm, and FAB Mass Spectroscopy FAB+ 868 m/e (m+1), FAB– 866 m/e (m–1).

Example 20

Synthesis of 3'-O-(diisopropylamino)-phosphinoacetic acid methyl ester-5'-O-di-ρ-anisylphenylmethyl thymidine 5'-DMT thymidine (10 grams, 18.4 mmoles) was reacted with acetic acid, (bis-(diisopropylamino)phosphino)-methyl ester (5.6 grams, 18.4 mmoles), in the presence of tetrazole (1.03 grains, 14.7 mmoles) for 48 hrs. The product was purified on silica gel by eluting the column with 50/50 hexanes/ethyl acetate, giving 11.55 grams (84% yield). Fractions from the column were collected and evaporated to a foam. The resulting purified phosphinoamidite was analyzed by $^{31}$P NMR, giving a set of diastereomers at δ 120.6 and δ 120.8 ppm, and FAB Mass Spectroscopy FAB+ 748 m/e (m+1), FAB– 746 m/e (m–1).

Example 21

Synthesis of 3'-O-(diisopropylamino)-phosphinoacetic acid dimethyl-β-cyanoethyl ester-5'-O-di-p-anisylphenylmethyl thymidine 5'-DMT thymidine (10 grams, 18.4 mmoles) was reacted with acetic acid, (bis(diisopropylamino)phosphino)-dimethylcyanoethylethyl ester (6.8 grams, 18.4 mmoles), in the presence of tetrazole (1.03 grams, 14.7 mmoles) for 48 hrs. The product was purified on silica gel by eluting the column with 50/50 hexanes/ethyl acetate, giving 12.88 grams (86% yield). Fractions from the column were collected and evaporated to a foam. The resulting purified phosphinoamidite was analyzed by $^{31}$P NMR, giving a set of diastereomers at δ 120.3 and δ 120.8 ppm, and FAB Mass Spectroscopy FAB+ 815 m/e (m+1), FAB– 813 m/e (m–1).

Example 22

Synthesis of 3'-O-(diisopropylamino)-phosphinoacetic acid methyl ester-5'-O-di-p-anisylphenylmethyl-N-4-benzoylcytosine 5'-DMT-N-4-benzoylcytosine (10 grams, 15.8 mmoles) was reacted with acetic acid, (bis-(diisopropylamino)phosphino)-methyl ester (4.8 grams, 15.8 mmoles), in the presence of tetrazole (0.89 grams, 12.64 mmoles) for 24 hrs. The product was purified on silica gel by eluting the column with 50/50 hexanes/ethyl acetate, giving 8.98 grams (68% yield). Fractions from the column were collected and evaporated to a foam. The resulting purified phosphinoamidite was analyzed by $^{31}$P NMR, giving a set of diastereomers at δ 121.1 and δ 122.0 ppm, and FAB Mass Spectroscopy FAB+ 837 m/e (m+1), FAB– 835 m/e (m–1).

Example 23

Synthesis of 3'-O-(diisopropylamino)-phosphinoacetic acid dimethyl-β-cyanoethyl ester-5'-O-di-p-anisylphenylmethyl-N-4-benzoylcytosine 5'-DMT-N-4-benzoylcytosine (10 grams, 15.8 mmoles) was reacted with acetic acid, (bis(diisopropylamino)phosphino)-dimethylcyanoethylethyl ester (5.86 grams, 15.8 mmoles), in the presence of tetrazole (0.89 grams, 12.64 mmoles) for 24 hrs. The product was purified on silica gel by eluting the column with 50/50 hexanes/ethyl acetate, giving 10.56 grams (74% yield). Fractions from the column were collected and evaporated to a foam. The resulting purified phosphinoamidite was analyzed by $^{31}$P NMR, giving a set of diastereomers at δ 121.5 and δ 121.1 ppm, and FAB Mass Spectroscopy FAB+ 904 m/e (m+1), FAB– 902 m/e (m–1).

Example 24

Synthesis of 3'-O-(diisopropylamino)-phosphinoacetic acid methyl ester-5'-O-di-p-anisylphenylmethyl-N-4-acetylcytosine 5'-DMT-N-4-acetylcytosine (10 grams, 17.5 mmoles) was reacted with acetic acid, (bis-(diisopropylamino)phosphino)-methyl ester (5.3 grams, 17.5 mmoles) in the presence of tetrazole (0.98 grams, 14.0 mmoles) for 24 hrs. The product was purified on silica gel by eluting the column with 50/50 hexanes/ethyl acetate, giving 11.12 grams (76% yield). Fractions from the column were collected and evaporated to a foam. The resulting purified phosphinoamidite was analyzed by $^{31}$P NMR, giving a set of diastereomers at δ 121.1 and δ 121.5 ppm, and FAB Mass Spectroscopy FAB+ 837 m/e (m+1), FAB– 835 m/e (m–1).

Example 25

Synthesis of 3'-O-(diisopropylamino)-phosphinoacetic acid dimethyl-β-cyanoethyl ester-5'-O-di-p-anisylphenylmethyl-N-4-acetylcytosine 5'-DMT-N-4-acetylcytosine (10 grams, 17.5 mmoles) was reacted with acetic acid, (bis-(diisopropylamino)phosphino)-dimethylcyanoethyl ester (6.5 grams, 17.5 mmoles), in the presence of tetrazole (0.98 grams, 14.0 mmoles) for 24 hrs. The product was purified on silica gel by eluting the column with 100% ethyl acetate, giving 11.48 grams (78% yield). Fractions from the column were collected and evaporated to a foam. The resulting purified phosphinoamidite was analyzed by $^{31}$P NMR, giving a set of diastereomers at δ 121.3 and δ 121.8 ppm, and FAB Mass Spectroscopy FAB+ 842 m/e (m+1), FAB– 840 m/e (m–1).

Example 26

Synthesis of 3'-O-(diisopropylamino)-phosphinoacetic acid methyl ester-5'-O-di-p-anisylphenylmethyl-N-9-benzoyl adenosine 5'-DMT-N-9-benzoyl adenosine (10 grams, 15.3 mmoles) was reacted with acetic acid, (bis-(diisopropylamino)phosphino)-methyl ester (4.7 grams, 15.3 mmoles), in the presence of tetrazole (0.86 grams, 12.24 mmoles) for 24 hrs. The product was purified on silica gel by eluting the column with 50/50 hexanes/ethyl acetate, giving 10.53 grams (80% yield). Fractions from the column were collected and evaporated to a foam. The resulting purified phosphinoamidite was analyzed by $^{31}$P NMR, giving a set of diastereomers at δ 120.7 and δ 121.6 ppm, and FAB Mass Spectroscopy FAB+ 861 m/e (m+1), FAB– 859 m/e (m–1).

Example 27

Synthesis of 3'-O-(diisopropylamino)-phosphinoacetic acid dimethyl-β-cyanoethyl ester-5'-O-di-p-anisylphenylmethyl-N-9-benzoyl adenosine 5'-DMT-N-9-benzoyl adenosine (10 grams, 15.3 mmoles) was reacted with acetic acid, (bis-(diisopropylamino)phosphino)-dimethylcyanoethyl ester (5.7 grams, 15.3 mmoles), in the presence of tetrazole (0.86 grams, 12.24 mmoles) for 24 hrs. The product was purified on silica gel by eluting the column with 50/50 hexanes/ethyl acetate, giving 10.64 grams (75% yield). Fractions from the column were collected and evaporated to a foam. The resulting purified phosphinoamidite was analyzed by $^{31}$P NMR, giving a set of diastereomers at δ 120.8 and δ 121.6 ppm, and FAB Mass Spectroscopy FAB+ 928 m/e (m+1), FAB− 926 m/e (m−1).

Example 28

Synthesis of 3'-O-(diisopropylamino)-phosphinoacetic acid methyl ester-5'-O-di-p-anisylphenylmethyl-N-2-isobutyrylguanosine 5'-DMT-N-2-isobutyrylguanosine (10 grams, 15.7 mmoles) was reacted with acetic acid, (bis-(diisopropylamino)phosphino)-methyl ester (4.8 grams, 15.7 mmoles), in the presence of tetrazole (0.88 grams, 12.56 mmoles) for 24 hrs. The product was purified on silica gel by eluting the column with 100% ethyl acetate, giving 10.97 grams (83% yield). Fractions from the column were collected and evaporated to a foam. The resulting purified phosphinoamidite was analyzed by $^{31}$P NMR, giving a set of diastereomers at δ 121.3 and δ 121.7 ppm, and FAB Mass Spectroscopy FAB+ 843 m/e (m+1), FAB− 841 m/e (m−1).

Example 29

Synthesis of 3'-O-(diisopropylamino)-phosphinoacetic acid dimethyl-β-cyanoethyl ester-5'-O-di-p-anisylphenylmethyl-N-2-isobutyrylguanosine 5'-DMT-N-2-isobutyrylguanosine (10 grams, 15.7 mmoles) was reacted with acetic acid, (bis-(diisopropylamino)phosphino)-dimethylcyanoethyl ester (5.8 grams, 15.7 mmoles), in the presence of tetrazole (0.88 grams, 12.56 mmoles) for 24 hrs. The product was purified on silica gel by eluting the column with 100% ethyl acetate, giving 12.70 grams (89% yield). Fractions from the column were collected and evaporated to a foam. The resulting purified phosphinoamidite was analyzed by $^{31}$P NMR, giving a set of diastereomers at δ 121.7 and δ 122.0 ppm, and FAB Mass Spectroscopy FAB+ 910 m/e (m+1), FAB− 908 m/e (m−1).

Example 30

Synthesis of 2'-O-(triisopropyl-silyloxymethyl)-3'-O-(diisopropylamino)-phoshino-acetic acid dimethyl-β-cyanoethyl ester-5'-O-di-p-anisylphenylmethyl-uridine 2'-O-(triisopropyl-silyloxymethyl)-5'-O-di-p-anisylphenylmethyl-uridine was prepared from 5'-O-di-p-anisylphenylmethyl-uridine and chloromethoxytriisopropylsilane using the conditions described by Wagner et. al. (1974), *J. Org. Chem*, 39:24 and Pitsch et al., WO. 99/09044, published Feb. 25, 1999. The protected nucleoside (5 grams, 6.8 mmol) was dissolved in anhydrous dichloromethane and reacted with acetic acid, (bis-(diisopropylamino)phosphino)-dimethylcyanoethyl ester (2.5 grams, 6.8 mmoles), in the presence of tetrazole (0.38 grams, 5.44 mmoles) for 24 hrs. The product was purified on silica gel by eluting the column with 50/50 hexanes/ethyl acetate giving 2.93 grams (43% yield). Fractions from the column were collected and evaporated to a foam. The resulting purified phosphinoamidite was analyzed by $^{31}$P NMR, giving a set of diastereomers at δ 120.8 and δ 126.8 ppm, and FAB Mass Spectroscopy FAB+ 1003 m/e (m+1), FAB− 1001 m/e (m−1).

Example 31

Synthesis of 2'-O-methyl-3'-O-(diisopropylamino)-phosphino-acetic acid dimethyl-β-cyanoethyl ester-5'-O-dip-anisylphenylmethyl-uridine 2'-O-methyl-5'-O-di-p-anisylphenylmethyl-uridine (10 grams, 18.3 mmol) was dissolved in anhydrous dichloromethane and reacted with acetic acid, (bis-(diisopropylamino)phosphino)-dimethylcyanoethyl ester (6.7 grams, 18.3 mmoles), in the presence of tetrazole (1.02 grams, 14.6 mmoles) for 24 hrs. The product was purified on silica gel by eluting the column with 50/50 hexanes/ethyl acetate, giving 8.80 grams (48% yield). Fractions from the column were collected and evaporated to a foam. The resulting purified phosphinoamidite was analyzed by $^{31}$P NMR, giving a set of diastereomers at δ 123.6 and δ 125.9 ppm, and FAB Mass Spectroscopy FAB+ 831 m/e (m+1), FAB− 829 m/e (m−1).

Example 32

Synthesis of thymidine-3'-O-acetic acid H-phosphonite

3'-O-(diisopropylamino)-phosphinoacetic acid dimethyl-β-cyanoethyl ester-5'-O-di-p-anisylphenylmethyl thymidine (1 gram, 1.2 mmol) was dissolved in anhydrous acetonitrile (10 ml). Tetrazole (0.1 gram, 1.4 mmol) was added to the solution along with 100 microliters of water. The product was evaporated to dryness and purified by preparative HPLC on a C-18 column. The product was redissolved in a minimum volume of acetonitrile and the dimethylcyanoethyl protecting group removed using concentrated ammonium hydroxide. The reaction mixture was evaporated to dryness and the product repurified by preparative HPLC on a C-18 column. The di-p-anisylphenylmethyl protecting group was removed by redissolving the product in 80% acetic acid of 90 min. The acetic acid was diluted with water and the product purified by HPLC. FAB Mass Spectroscopy FAB+ 349 m/e (m+1), FAB− 347 m/e (m−1).

Example 33

General Method for Synthesis of Phosphonoacetate Oligonucleotides

The chemical synthesis of phosphonoacetate oligonucleotides was accomplished using an ABI model 394 automated DNA synthesizer from PE Biosystems, Foster City Calif. The synthesis cycle used was adapted from a standard one micromolar β-cyanoethylphosphoramidite DNA synthesis cycle (FIG. 1). The coupling wait-time was increased to 1998 seconds. The oxidation step was accomplished prior to the capping step. The 3'-O-(diisopropylamino)-phosphinoacetic acid dimethylcyanoethyl ester-5'-O-di-p-anisylphenylmethyl protected nucleosides were dissolved in anhydrous acetonitrile at a concentration of 0.1M. The exocyclic amine groups were protected as follows: adenosine was protected by a benzoyl group; cytidine was protected with an acetyl group; and guanosine was protected with an isobutyryl group. Freshly sublimed tetrazole was used as an activator and was dissolved in anhydrous acetonitrile at a concentration of 0.45M. Trichloroacetic acid, 3% (wt/vol), dissolved in anhydrous dichloromethane, was used to deprotect the 5'-O-di-p-anisylphenylmethyl groups prior to each round of coupling. Capping was accomplished using a two-part capping solution, designated cap A and cap B. Cap A: 10% acetic anhydride in anhydrous tetrahydrofuran. Cap B: 0.625% (wt/vol) 4-N,N-dimethylaminopyridine in anhydrous pyridine. Oxidation of the nascent internucleotide acetic acid phosphonite to the phosphonate was accomplished using (1S)-(+)(10-camphorsufonyl)-oxaziridine (CSO) dissolved in anhydrous acetonitrile at a concentration of 0.1M. The oxidation wait time was increased to 180 seconds.

Post-synthesis, the control pore glass (CPG) was washed with anhydrous acetonitrile for 60 seconds and then flushed with a stream of argon until dry. The column was then fitted with two 1 mL syringes. The CPG was exposed to a 1.5% 1,8-diazabicyclo[5.4.0]undec-7-ene (DBU) solution (15 µl in 1 mL of anhydrous acetonitrile) by pushing the solution back and forth with the syringe plungers. The reaction was allowed to proceed for 30 minutes to remove the dimethylcyanoethyl groups. The DBU solution was removed and discarded. The CPG was then washed via syringe action in the following manner: 20 mL anhydrous acetonitrile, followed by 2 mL of 400 mM Tris-HCl. The CPG was flushed with argon until dry and then transferred to a Teflon-lined screw-cap glass vial. The phosphonoacetate oligonucleotide was cleaved from the glass support, and the exocyclic amine-protecting groups were removed using a 40% solution of methylamine in water. Deprotection and cleavage were carried out at 55° C. for 15 minutes and the vial was subsequently cooled to room temperature, and evaporated to dryness under vacuum.

Example 34

General Method for Synthesis of Phosphonothioacetate Oligonucleotides

Figure 2:
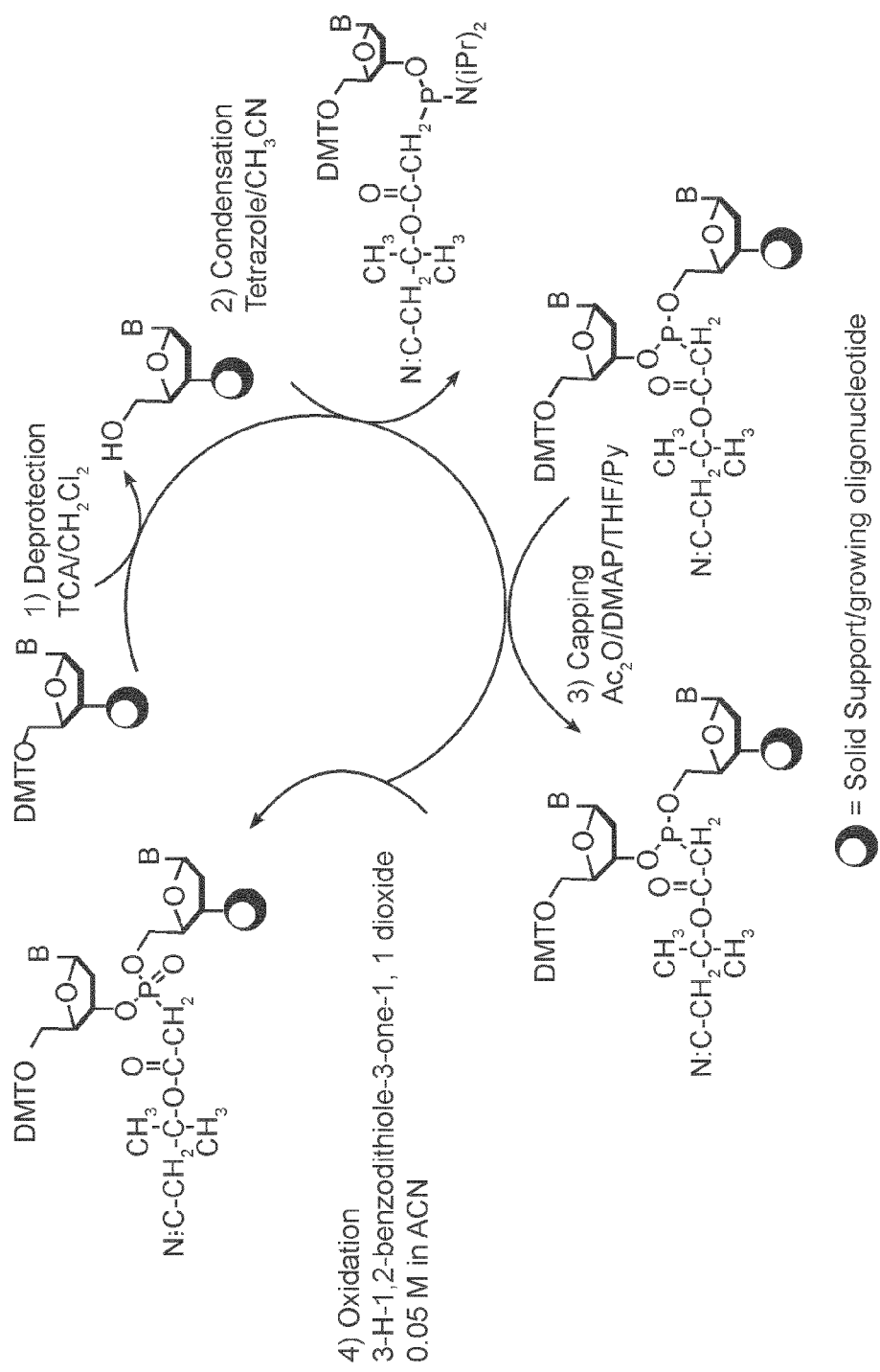
FIG. 2 schematically illustrates synthesis of phosphonothioacetate polynucleotides on a solid support, as described in detail in Example 34.

The chemical synthesis of phosphonothioacetate oligonucleotides was accomplished using an ABI model 394 automated DNA synthesizer and the chemistry illustrated schematically in FIG. 2. The synthesis cycle used was adapted from the standard one micromolar β-cyanoethylphosphoramidite DNA synthesis cycle. The coupling wait-time was increased to 2 times 999 seconds. The oxidation step was accomplished prior to the capping step. The 3'-O-(diisopropylamino)-phosphinoacetic acid dimethylcyanoethyl ester-5'-O-di-p-anisylphenylmethyl protected nucleosides were dissolved in anhydrous acetonitrile at a concentration of 0.1M. The exocyclic amine groups were protected as follows: adenosine was protected by a benzoyl group; cytidine was protected with an acetyl group; and guanosine was protected with an isobutyryl group. Freshly sublimed tetrazole was used as an activator and was dissolved in anhydrous acetonitrile at a concentration of 0.45 M. Trichloroacetic acid, 3% (wt/vol), dissolved in anhydrous dichloromethane, was used to deprotect the 5'-O-di-p-anisylphenylmethyl groups prior to each round of coupling. Capping was accomplished using a two part capping solution, designated cap A and cap B. Cap A: 10% acetic anhydride in anhydrous tetrahydrofuran. Cap B: 0.625% (wt/vol) 4-N,N-dimethylaminopyridine in anhydrous pyridine. Oxidation of the nascent internucleotide acetic acid phosphonite to the thiophosphonate was accomplished using -1,1-dioxide 3H-1,2-benzodithiole-3-one-1,1-dioxide dissolved in anhydrous acetonitrile at a concentration of 0.05M. The oxidation wait time was increased to 60 seconds. Post-synthesis, the CPG was washed with anhydrous acetonitrile for 60 seconds and then flushed with a stream of argon until dry. The column was then fitted with two 1 mL syringes, The CPG was exposed to a 1.5% DBU solution (15 µl in 1 mL of anhydrous acetonitrile) by pushing the solution back and forth with the syringe plungers. The reaction was allowed to proceed for 30 minutes to remove the dimethylcyanoethyl groups. The DBU solution was removed and discarded. The CPG was then washed via syringe action in the following manner: 20 mL anhydrous acetonitrile, followed by 2 mL of 400 mM Tris-HCl. The CPG was flushed with argon until dry and then transferred to a Teflon-lined, screw-cap glass vial. The phosphonothioacetate oligonucleotide was cleaved from the glass support, and the exocyclic amine-protecting groups were removed using a 40% solution of methylamine in water. Deprotection and cleavage were carried out at 55° C. for 15 minutes and the vial was subsequently cooled to room temperature for further purification.

Example 35

HPLC Purification of Phosphonoacetate and Thiophosphonoacetate Oligonucleotides

Phosphonoacetate and thiophosphonoacetate oligonucleotides were purified by reverse-phase HPLC using the 5'-di-p-anisylphenylmethyl protecting group (trityl) for hydrophobic affinity. After cleavage from CPG, the methylamine solution was cooled to room temperature and filtered through a Pasteur pipette (fitted with a plug of glass wool) into a separate tube. The CPG was washed twice with 0.5 mL of water, filtered, and the combined volumes were concentrated to dryness under vacuum. The crude oligonucleotide mixture was dissolved in 0.5 mL of water for purification by HPLC. Preparative HPLC utilized a Zorbax 300SB-C18 column (9.4 mm ID×25 cm). Eluents were (a) 100 mM triethylammonium acetate, pH 8.0, and (b) acetonitrile. The following gradient conditions were used to elute the trityl-on oligonucleotides: 0-2 min, 8% B; 2-27 minutes, 8 to 20% B; and finally 27-52 min, 20 to 80% B. The flow rate was 1.2 mL/min. The desired fractions were collected, concentrated under vacuum, and dissolved in 100 µl of 10 mM Tris-HCl, pH 8. The trityl group was removed by treatment with 80% acetic acid (1 mL). After 1 hour, the solution was concentrated to dryness and dissolved in 50 mM triethylammonium acetate, pH 8 (0.5 mL). Finally, preparative HPLC, using the Zorbax 300SB-C18 column (9.4 mm ID×25 cm), was utilized to isolate and desalt the fully deprotected oligonucleotides. The elution profile used was as follows: 0% B, for 30 min; then a gradient of 0 to 80% B, from 30 to 50 min. The flow rate was 1.2 mL/min.

Example 36

Figure 3:
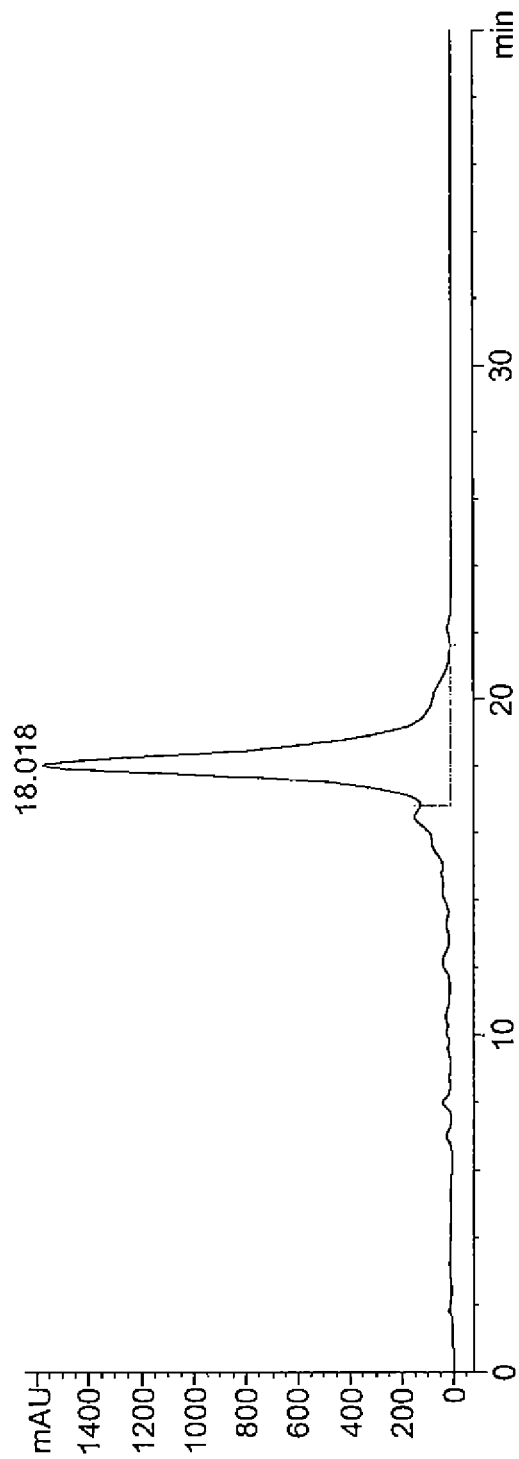
FIGS. 3 and 4 illustrate the results of ion exchange HPLC of 18-mer mixed sequence phosphonoacetate and phosphonothioacetate oligonucleotides, respectively, as described in Example 36.
Figure 4:
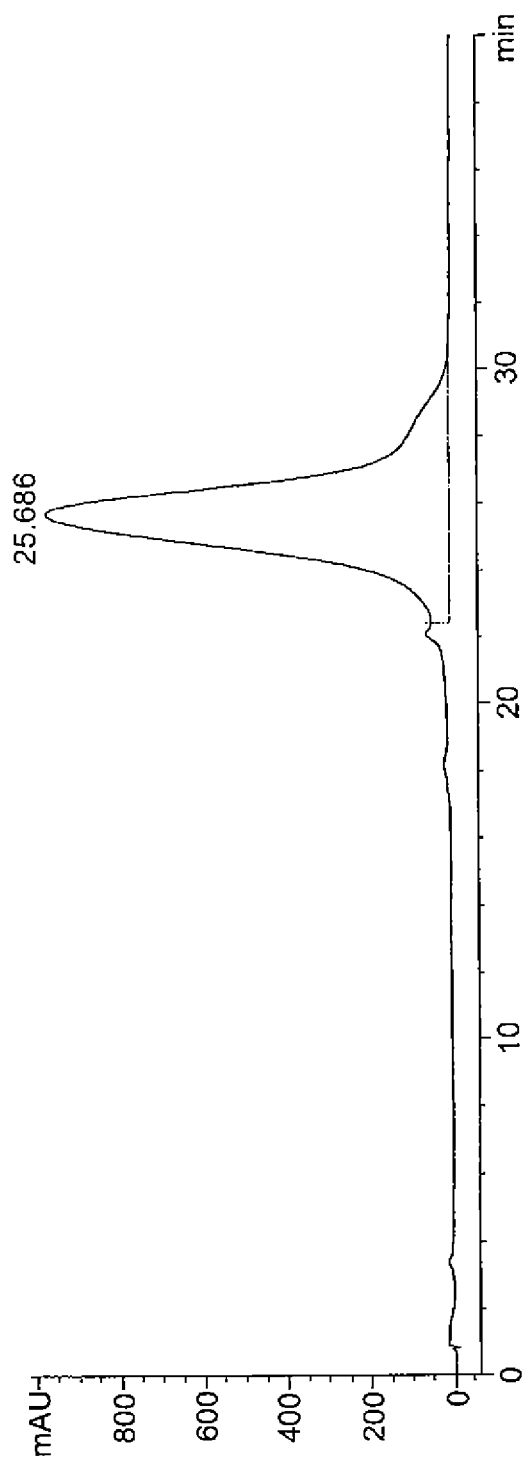

Ion Exchange HPLC Analysis of 18-mer Mixed Sequence Phosphonoacetate and Phosphonothioacetate Oligonucleotides Mixed sequence 18-mer oligonucleotides 5'-CTCAAGTGGGCTGGTGAC-3' were synthesized using the synthesis cycles described for phosphonoacetates (Example 34, FIG. 1) and phosphonothioacetates (Example 35, FIG. 2) and purified by reverse-phase HPLC. These sequences were analyzed for synthetic yield of full-length product by ion exchange HPLC. The HPLC was preformed using a Resource Q column (6.4 mm ID×30 mm) obtained from Amersham/Pharmacia. Eluents were (a) 10 mM NaOH/80 mM NaBr and (b) 10 mM NaOH/1.5M NaBr. The gradient was 0% A to 100% B in 45 minutes at a flow rate of 1.5 mL/min. For both syntheses, per cycle coupling efficiency of greater than 97% per cycle was obtained. Results are shown in FIGS. 3 and 4.

Purified sequences were evaporated to dryness and redissolved in $D_2O$ for $^{31}P$ NMR analysis of the phosphorus backbone using a Varian VXR-300 broadband NMR. Integration of the phosphorus signals demonstrated greater than 98% phosphonoacetate or phosphonothioacetate internucleotide linkages in the purified products.

Example 37

MALDI-TOF Mass Spectroscopy

Figure 5:
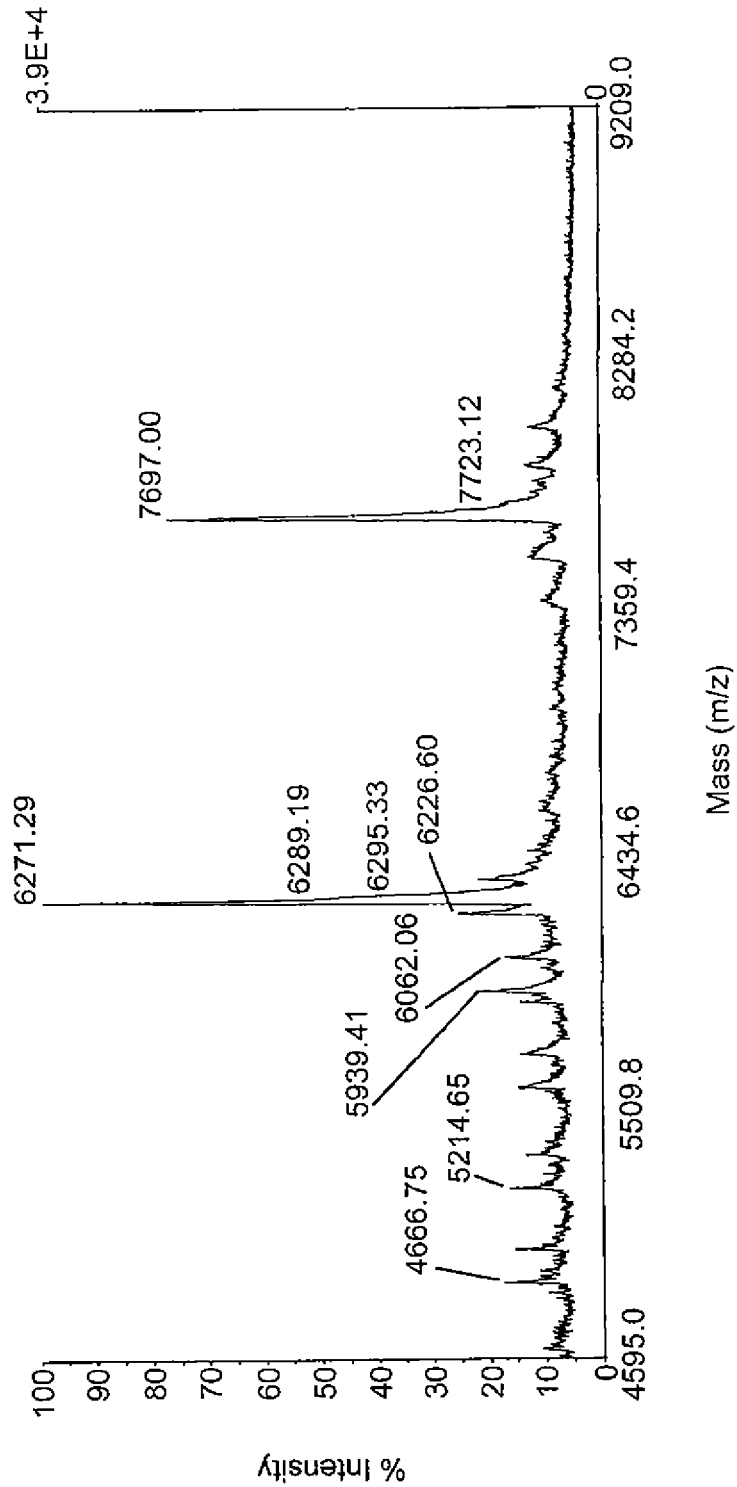
FIGS. 5 and 6 provide the results of matrix-assisted laser desorption ionization time of flight (MALDI-TOF) spectroscopic analysis on mixed sequence 18-mer phosphonoacetate and phosphonothioacetate oligonucleotides, respectively, as described in detail in Example 37.
Figure 6:
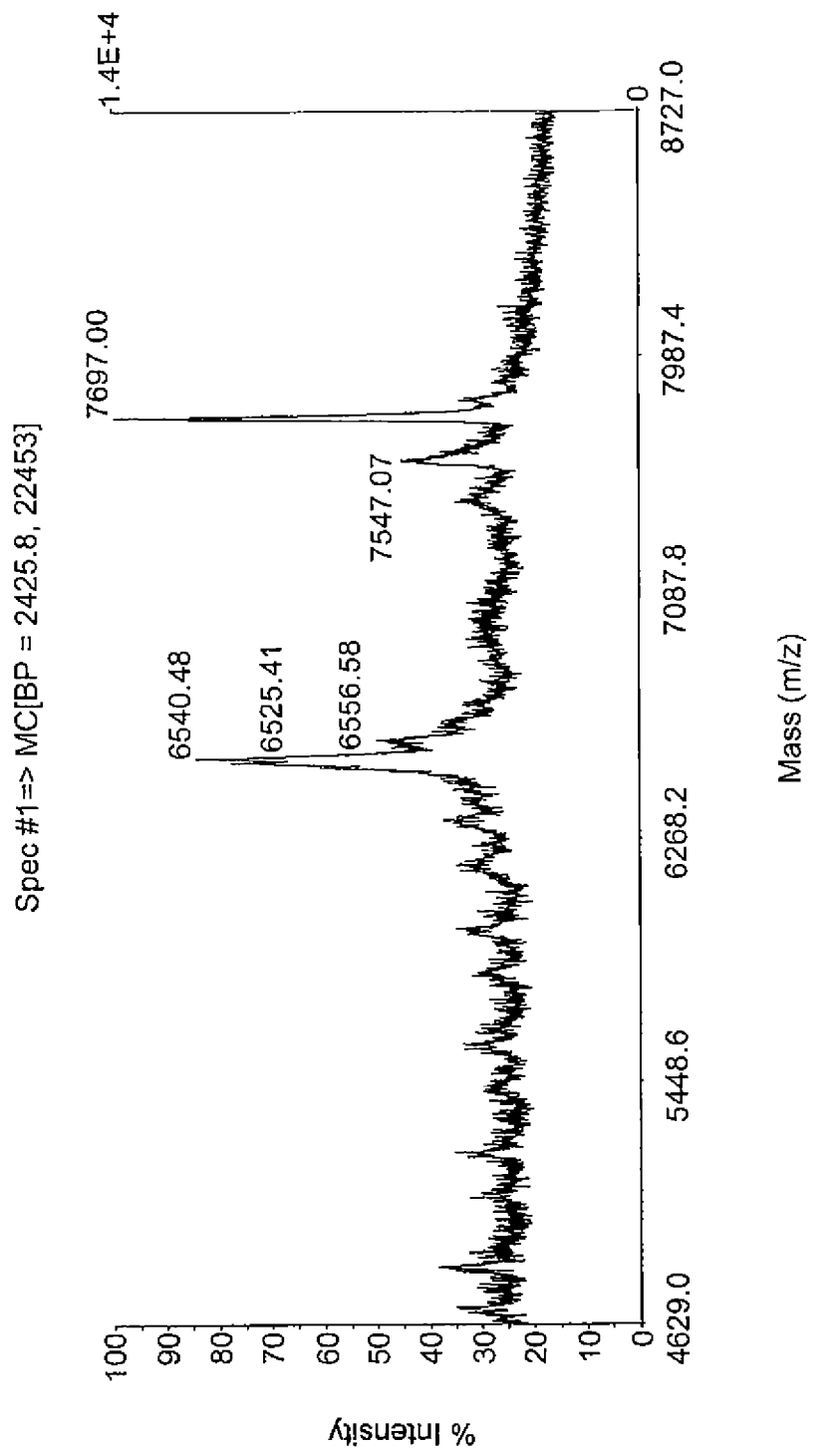

Matrix-assisted laser desorption ionization time of flight (MALDI-TOF) spectroscopic analysis was performed on the mixed sequence 18-mer phosphonoacetate and phosphonothioacetate oligonucleotides. Results are shown in FIGS. 5 and 6, respectively. The analysis was performed on a PerSeptive Biosystems Voyager Biospectrometry Workstation. The carboxylic acid modified oligonucleotides were concentrated to dryness and dissolved in isopropanol/water (1:1) to a final concentration of 200 pmol/µl. Samples were prepared as described in the Sequazyme Oligonucleotide Sequencing Kit (PerSeptive Biosystems) with the following modifications: 1 µl of oligonucleotide, 1 µl 25-mer DNA standard, 1 µl of ammonium citrate buffer and 7 µl of matrix were combined on a layer of parafilm coated with ammonium cation exchange beads. After pipetting the solution over the beads for 60 seconds, 5 µl was transferred to a gold-plated 100 well plate. The MALDI-TOF measurements were observed in the positive ion mode. The calculated mass for the mixed sequence 18-mer phosphonoacetate was 6270.2, and the observed mass was 6271.5 (FIG. 5). The calculated mass for the mixed sequence 18-mer phosphonothioacetate was 6542.1, and the observed mass was 6541.2 (FIG. 6).

Example 38

Evaluation of Nuclease Resistance of Phosphonoacetate and Phosphonothioacetate Oligonucleotides This example describes an evaluation of the nuclease stabilities of oligodeoxynucleotides (ODNs) containing phosphonoacetate and phosphonothioacetate internucleotide bonds. Nuclease resistance of these modified oligonucleotides was evaluated using Snake Venom Phosphodiesterase and DNase I, as follows.

ODN Synthesis and Purification: Control ODNs and phosphonoacetate ODNs were synthesized by solid-phase phoshoramidite methods on controlled pore glass using an automated synthesizer (Applied Biosystems model 394, Foster City, Calif.) substantially as described in Example 34. Phosphorothioate ODNs were prepared a similar manner using 3H-1,2-benzodithiole-3-1,1 dioxide for sulfurization of the nascent phosphite internucleotide bonds (Glen Research, Sterling, Va.), as described in Example 34, wherein the sulfurizing reagent was dissolved in anhydrous acetonitrile (0.05 M) and the oxidation wait time was 45 seconds. Phosphonoacetate and phosphonothioacetate ODNs were purified as described in Examples 34 and 35. Commercially obtained phosphoramidite synthons were used to incorporate a phosphodiester linkage on the 5'-end of the phosphonoacetate and phosphonothioacetate ODNs. Autoradiographic imaging was performed on a Molecular Dynamics Phosphorimager (Storm 820).

Radiolabeling of Oligodeoxynucleotides: ODNs were 5' end-labeled using $\gamma$-$^{32}P$ ATP and T4 polynucleotide kinase (Wu et al., "Purification and Sequence Analysis of Synthetic Oligodeoxyribonucleotides," in *Oligonucleotide Synthesis: A Practical Approach*, Gait, Ed. (Oxford University Press, 1990)). Phosphorylation of the phosphonoacetate and phosphonothioacetate ODNs was achieved using similar conditions and a 3 to 4-fold increase in the number of equivalents of $\gamma$-$^{32}P$ ATP. The radiolabeled ODNs were purified by gel electrophoresis and ethanol precipitation. Quantitation of radioactivity was accomplished using ImageQuant software (version 5.1).

MALDI-TOF mass spectroscopy. Matrix-assisted laser desorption ionization time of flight (MALDI-TOF) spectroscopic analysis was performed on a PerSeptive Biosystems Voyager Biospectrometry Workstation as described in Example 37.

Exonuclease Stability: Exonuclease digestion experiments were carried out using Phosphodiesterase I from *Crotalus adamanteu* (Cummings et al. (1996) *Nucleic Acids Research* 23:2019-2024). The assays were performed using a mixture of oligonucleotides labeled with $^{32}P$ at the 5'-end (100,000 cpm) and unlabeled oligonucleotide (40 pmol) in a buffer containing 50 mM Tris-HCl, pH 8.5, 72 mM NaCl and 14 mM $MgCl_2$. Enzyme was added to a final concentration of 0.5 units/mL (40 µl total reaction volume). The reaction mixture was overlaid with 25 µl of mineral oil and incubated at 37° C. Aliquots (3.5 µl) were removed and quenched by adding 7M urea in TBE buffer (12 µl) and heating to 95° C. for 5 minutes. Time points were taken at 0, 1, 3, 7, and 18 hours after the addition of enzyme. Samples were stored at −70° C. until analysis by PAGE (20%, containing 7M urea).

Endonuclease Stability: Endonuclease digestion experiments were carried out using DNase I (Boehringer-Mannheim). The assays were performed using a mixture of oligodeoxynucleotide labeled with $^{32}P$ at the 5'-end (100,000 cpm) and unlabeled oligodeoxynucleotide (40 pmol) in a buffer containing 40 mM Tris-HCl, pH 7.5, 6 mM $MgCl_2$. Slight excess of the complementary DNA strand (1.2 eq.) was added and the mixture was heated to 95° C. for 5 minutes then chilled on ice for 30 minutes. Enzyme was added to a final concentration of 1 unit/µl (40 µl total reaction volume). The reaction mixture was overlayed with 25 µl of mineral oil and incubated at 37° C. Aliquots (3.5 µl) were removed and quenched by adding 7M urea in TBE buffer (12 µl) and heating to 95° C. for 5 minutes. Time points were taken at 0, 1, 3, 7, and 18 hours after the addition of enzyme. Samples were stored at −70° C. until analysis by PAGE (20%, containing 7M urea).

Four 18-mer mixed sequence ODNs were synthesized, each having the sequence 5'-CTCAAGTGGGCTGGTGAC-3', with one ODN containing internucleotide phosphonoacetate linkages, one ODN containing internucleotide phosphonothioacetate linkages, another ODN containing internucleotide phosphorothioate linkages, and a fourth ODN containing internucleotide phosphodiester linkages. The ODNs were synthesized, purified, and their identity verified by MALDI-TOF mass spectroscopy using the above procedures. Results of the MALDI-TOF spectroscopic evaluation are set forth in Table 1:

TABLE 1

| Internucleotide Bond | Calculated Mass | Observed Mass |
| --- | --- | --- |
| Phosphonoacetate | 6227.9 | 6228.8 |
| Phosphodiester | 5555.8 | 5555.1 |
| Phosphonothioacetate | 6525.9 | 6524.3 |
| Phosphorothioate | 5827.8 | 5829.5 |

The digestion reactions were monitored by radiolabeling the 5'-end of the ODN using $\gamma$-$^{32}$P ATP and T4 polynucleotide kinase. Attempts to radiolabel fully modified phosphonoacetate and phosphonothioacetate ODNs were unsuccessful using T4 Polynucleotide Kinase. In order to phosphorylate these modified ODNs, it was necessary to synthesize the sequences containing one phosphodiester internucleotide linkage immediately 3' to the 5'-end of the molecule. Phosphorylation of these modified ODNs required 4-fold excess $^{32}$P-ATP with respect to the conditions used for unmodified DNA.

Figure 7:
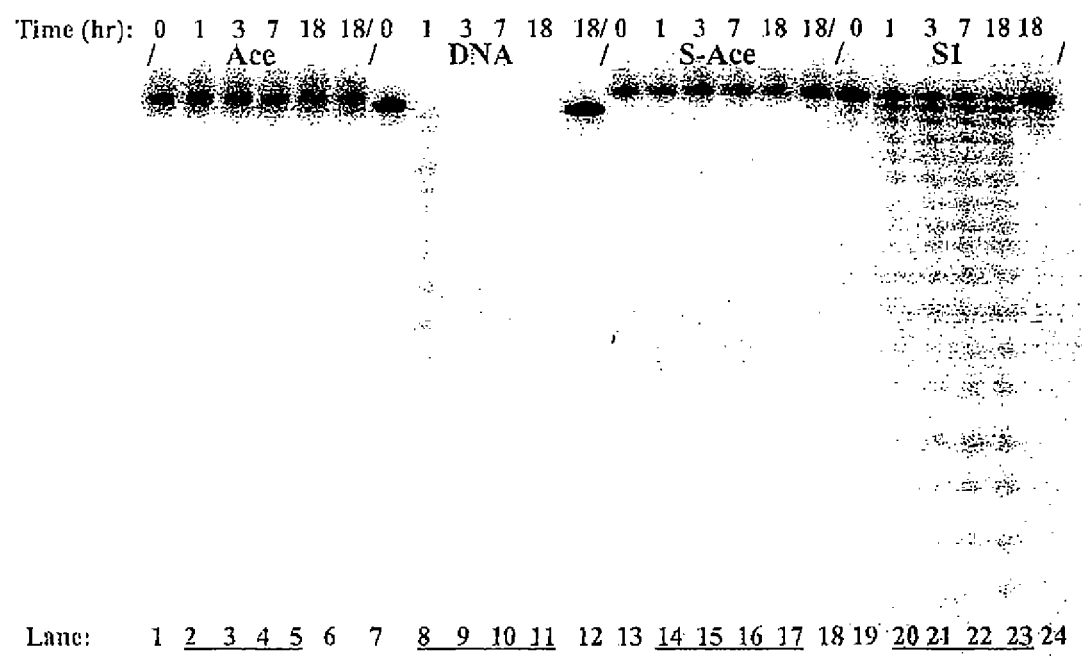
FIG. 7 is an autoradiogram of $^{32}$P-5'-end labeled oligodeoxynucleotide 18-mers in the presence of snake venom phosphodiesterase, as described in Example 38.

The phosphonoacetate, phosphonothioacetate, phosphorothioate, and phosphodiester ODNs were incubated with snake venom phosphodiesterase (SVP) and their degradation was monitored as a function of time. Aliquots were removed from the reaction mixture and quenched by addition of 7M urea followed by heating to 95° C. for 5 minutes. Each aliquot was then stored at –70° C. until analysis. Control experiments were performed without enzyme to compare full-length oligonucleotides to SVP-mediated hydrolysis products. The reaction products were separated and analyzed by gel electrophoresis and imaged by autoradiography. FIG. 7 shows the results observed for the ODNs when exposed to SVP. No detectable degradation products were observed for the reactions containing the phosphonoacetate ODN ("Ace," lanes 2 through 5). The phosphodiester ODN substrate was completely degraded within 60 minutes ("DNA," lane 8). The phosphonothioacetate ODN gave no detectable hydrolysis products through the course of the experiment ("S-Ace," lanes 14 through 17). Lanes 20 through 23 show the hydrolysis products for the phosphorothioate substrate ("S1") upon incubation with SVP. After 60 minutes, approximately 65% of the full-length ODN was remained, and after 18 hours 40% full-length ODN remained.

Figure 8:
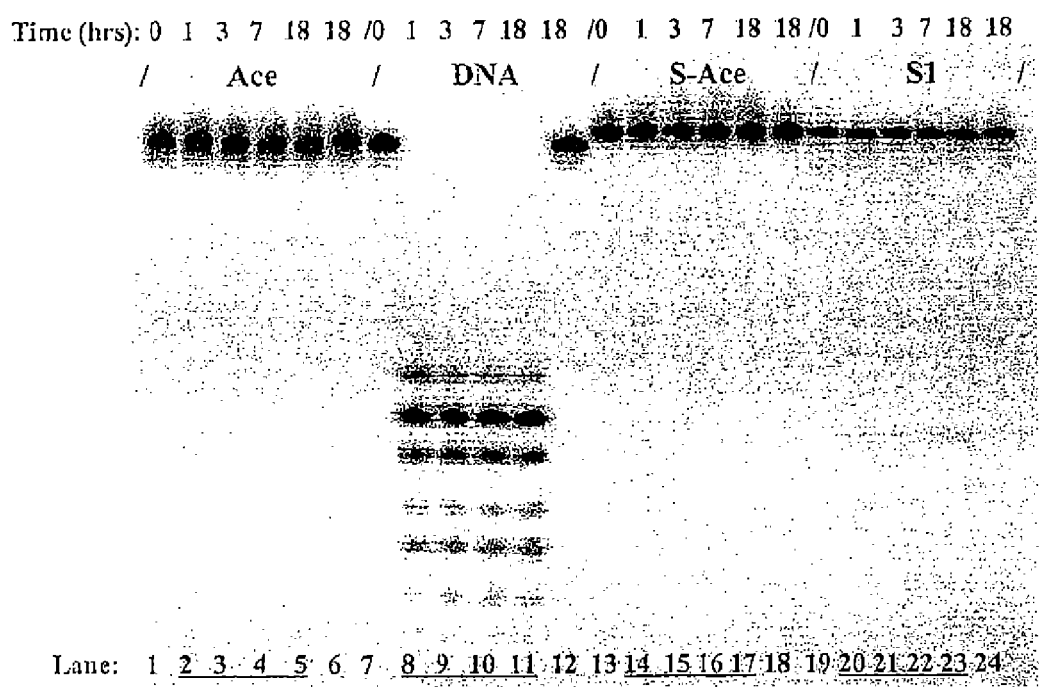
FIG. 8 is an autoradiogram of duplexes of $^{32}$P-5'-end labeled oligodeoxynucleotide 18-mers in the presence of DNaseI, as described in Example 38.

To characterize the phosphonoacetate and phosphonothioacetate ODNs' stability towards endonuclease, the radiolabeled modified ODNs were hybridized to complementary sequences of unmodified ODNs and incubated with DNase I. Duplexes were pre-formed by mixing the various ODNs separately with a non-radiolabeled complementary 18-mer DNA strand. The mixtures were heated to 95° C. for 5 minutes followed by slow cooling and incubation on ice for 30 minutes. The mixture was equilibrated to room temperature, DNase I added, and the reaction monitored as a function of time. Control experiments were performed without enzyme to compare full-length oligonucleotides to DNase I-mediated hydrolysis products. The reaction products were resolved by gel electrophoresis and imaged by autoradiography. FIG. 8 shows the typical results of exposure to DNase I for the 18-mer duplexes tested. Analysis of lanes 2 through 5 show no degradation products for the phosphonoacetate ("Ace") oligodeoxynucleotide substrate upon incubation with DNase I, even after exposure to the enzyme for 18 hours. However, analysis of lane 8 ("DNA") shows that the full-length DNA substrate was completely degraded within 1 hour and that several hydrolysis fragments were consistently observed during the assay. Alternatively, evaluation of lanes 14 through 17 reveal that no hydrolysis products were observed for the phosphonothioacetate ("S-Ace") analog during the time-course of the experiment. For the phosphorothioate substrate ("S1," lanes 20 through 23) some hydrolysis products appeared through out the time course of the experiment (approximately 12% degraded over 18 hours).

The results indicate that phosphonoacetate and phosphonothioacetate-containing oligodeoxynucleotides are highly nuclease-resistant.

Example 39

Evaluation Phosphonoacetate and Phosphonothioacetate Oligonucleotide-RNA Duplexes as Substrates for RNaseH This example evaluates the ability of phosphonoacetate and phosphonothioacetate ODNs to bind to complementary RNA and subsequently act as substrates for *E. coli* RNaseH1, i.e., directing the hydrolysis of complementary RNA in the presence of the RnaseH. Four ODNs were synthesized as in the preceding example, i.e., 18-mer mixed sequence ODNs each having the sequence 5'-CTCAAGTGGGCTGGTGAC-3', with one ODN containing internucleotide phosphonoacetate linkages, one ODN containing internucleotide phosphonothioacetate linkages, another ODN containing internucleotide phosphorothioate linkages, and a fourth ODN containing internucleotide phosphodiester linkages. The ODNs were purified, and their identity verified by MALDI-TOF mass spectroscopy using the procedures of the preceding example.

Hybridization of oligonucleotides to complementary RNA: Hybridization studies were performed using equimolar amounts (1 µM) of the phosphonoacetate, phosphonothioacetate, phosphorothioate, 2'-O-methyl modified or phosphodiester oligonucleotides with the complementary oligoribonucleotide strand. Experiments were performed using two different buffer conditions: 1) 1M sodium chloride in phosphate-buffered saline; and 2) RNaseH buffer conditions.

Melting Point Measurements: Melting points, $T_m$s, for the 18-mer heteroduplexes were determined on a Varian Cary 1E UV-visible spectrometer. The absorbance at 260 nm was measured while the temperature of the sample was increased at rate of 1.0° C./min. Phosphonoacetate, phosphonothioacetate, phosphorothioate, 2'-O-Methyl modified, and phosphodiester oligonucleotides were separately mixed with complementary RNA in a 1 mL cuvette and the $T_m$ determined as the maximum of the first derivative of the melting curve. Typical concentrations were 1 µM in each strand, pH 7.2 and contained 1 mM EDTA, 10 mM Na$_2$HPO$_4$+1.0M NaCl. Melting curves were also determined using *E. coli* RNaseH1 buffer conditions: 20 mM HEPES-KOH (pH 7.8), 50 mM KCl, 10 mM MgCl$_2$, 1 mM DTT.

Hydrolysis of RNA hetero-duplexes with *E. coli* RNaseH1. Complementary RNA was 5' end-labeled using $\gamma$-$^{32}$P ATP and T4 polynucleotide kinase (Wu et al., supra). A mixture of 5' $^{32}$P labeled RNA (100,000 cpm/reaction) and unlabeled RNA (125 pmol) were mixed with 100 pmol of complementary oligonucleotide in a buffer containing 20 mM HEPES-KOH (pH 7.8), 50 mM KCl, 10 mM MgCl$_2$, 1 mM DTT, and 40 units of RNasin (Promega) and incubated at 37° C. for 60 minutes. Two units of *E. coli* RNaseH1 (Promega) were added, and the reaction was allowed to proceed for four hours at 37° C. (20 µl total reaction volume). Aliquots of the reaction mixture (3.5 µl) were quenched with 7M urea in TBE buffer (12 µl) and stored at –70° C. until analysis by gel electrophoresis (20%, 19:1 crosslink).

Figure 9:
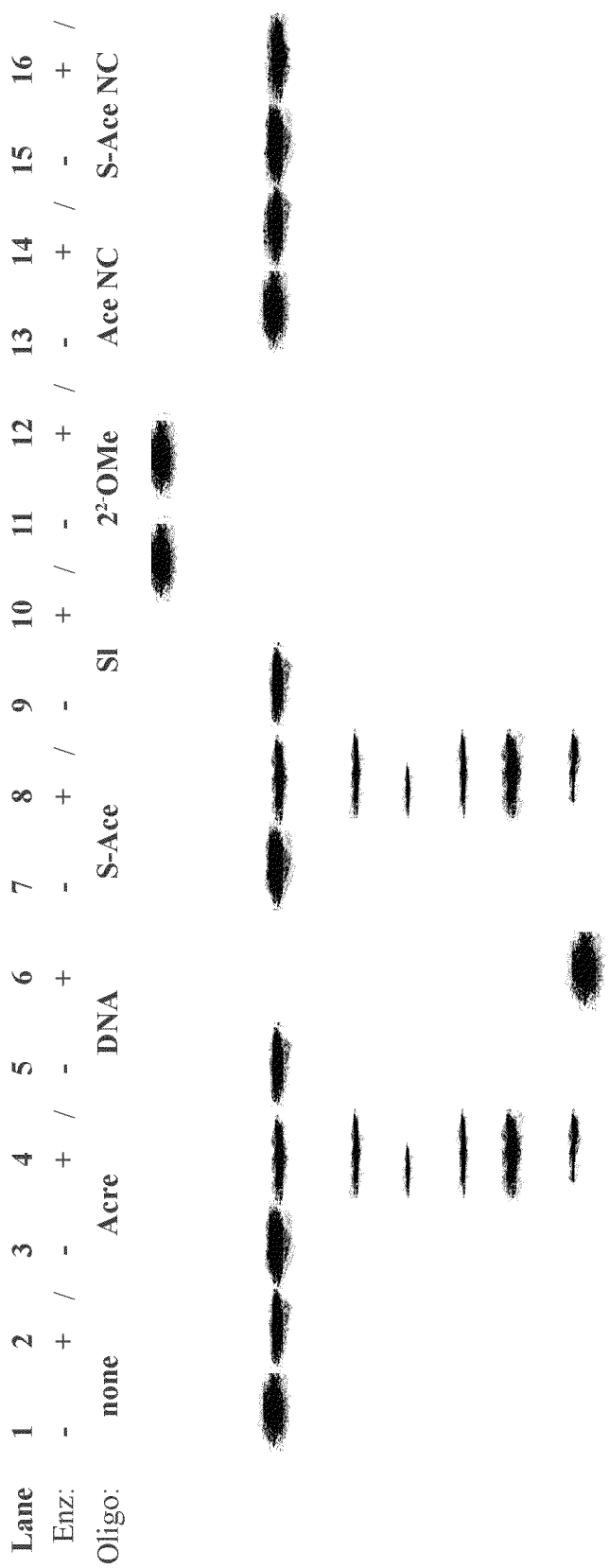
FIG. 9 is an autoradiogram of $^{32}$P-5'-end labeled RNA in the presence of complementary oligonucleotides and *E. coli* RNaseH1, as described in Example 39.

RNaseH1 Activity of Phosphonoacetate and Phosphonothioacetate-RNA heteroduplexes: The RNaseH experiments were monitored by radiolabeling the 5'-end of the RNA strand using $\gamma$-$^{32}$P ATP and T4 polynucleotide kinase (Wu et al., supra). Phosphonoacetate, phosphonothioacetate, phosphorothioate, 2'-O-methyl sugar-modified phosphodiester and phosphodiester oligonucleotides were separately mixed with complementary RNA and allowed to equilibrate at 37° C. for one hour. Reactions were initiated by the addition of RNaseH and incubated at 37° C. for four hours. Aliquots were removed from the reaction mixture and quenched by addition of 7M urea in TBE buffer followed by heating to 95° C. for 5 minutes. Each aliquot was then stored on ice until analysis. The reaction products were resolved by gel electrophoresis and imaged by autoradiography. Results from a typical RNaseH1 experiment are shown in FIG. 9. Each oligonucleotide was tested in the presence and absence of the enzyme. Examination of lane 4 shows the hydrolysis of complementary RNA when hybridized to the phosphonoacetate ODN in the presence of E. coli RNaseH1. The RNA was degraded by approximately 66% during the course of the experiment. Under the same conditions, no hydrolysis products were observed when the RNA was incubated with non-complementary phosphonoacetate ODN (lane 14). When exposed to RNaseH1 approximately 67% of the RNA was degraded in the presence of complementary phosphonothioacetate ODN (lane 8). Furthermore, the presence of the non-complementary phosphonothioacetate ODN did not result in any significant hydrolysis products when incubated with RNaseH1 (lane 16). When the phosphodiester ODN-RNA and phosphorothioate ODN-RNA duplexes were incubated with RNaseH1 nearly 100% of the starting material was converted to hydrolysis products. In the presence of complementary 2'-O-methyl oligoribonucleotide, no RNA hydrolysis products were detected. The migration patterns of the radiolabeled RNA in the 2'-O-methyl modified-RNA lanes were congruent with duplex oligonucleotide structures as assessed by native gel electrophoresis of the heteroduplexes. No hydrolysis products were generated in the absence of a complementary oligonucleotide strand (lane 2).

hydrocarbyl, or $R^5$ and $R^6$ are linked to form a substituted or unsubstituted, five- or six-membered nitrogen-containing heterocycle, D is O, S or NH, and L is a heteroatom-protecting group, unsubstituted hydrocarbyl, substituted hydrocarbyl, heteroatom-containing hydrocarbyl, or substituted heteroatom containing hydrocarbyl; X is O, S, NH, or $NR^7$ wherein $R^7$ is hydrocarbyl, substituted hydrocarbyl, heteroatom-containing hydrocarbyl or substituted heteroatom-containing hydrocarbyl; n is zero or 1; Y is —(Y')m-($CR^8R^9$)— wherein m is zero or 1, Y' is hydrocarbylene, substituted hydrocarbylene, heteroatom-containing hydrocarbylene, or substituted heteroatom-containing hydrocarbylene, wherein $R^8$ and $R^9$ are independently selected from the group consisting of hydrogen, hydrocarbyl, substituted hydrocarbyl, heteroatom-containing hydrocarbyl and substituted heteroatom-containing hydrocarbyl; and Z is O, S, NH or $NR^{10}$ wherein $R^{10}$ is as defined for $R^7$ wherein in any substituted moiety at least one hydrogen atom bound to a carbon atom is replaced by at least one of the following: alkoxy, thio, thioester, halo, amino, nitrile, nitro, sulfonyl, phosphoro, carboxyl, carbonyl, silyl and thienyl.

2. The compound of claim 1, wherein $R^1$ is selected from the group consisting of β-cyanoethyl, methyl-β-cyanoethyl, dimethyl-β-cyanoethyl, phenylsulfonylethyl, methyl-sulfonylethyl, p-nitrophenylsulfonylethyl, 2,2,2-trichloro-1,1-dimethylethyl, 2-(4-pyridyl)ethyl, 2-(2-pyridyl)ethyl, allyl, 4-methylene-1-acetylphenol, -thiobenzoylethyl, 1,1,1,3,3,3-

I claim:
1. A compound having the structural formula (I),

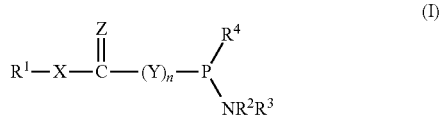

(I)

wherein $R^1$ is a protecting group removable by an elimination reaction; $R^2$ and $R^3$ are independently selected from the group consisting of hydrocarbyl, substituted hydrocarbyl, heteroatom-containing hydrocarbyl and substituted heteroatom-containing hydrocarbyl, or $R^2$ and $R^3$ are linked to form a substituted or unsubstituted, five- or six-membered nitrogen-containing heterocycle; $R^4$ is $NR^5R^6$, halogen or DL, wherein $R^5$ and $R^6$ are independently selected from the group consisting of hydrocarbyl, substituted hydrocarbyl, heteroatom-containing hydrocarbyl and substituted heteroatom-containing hexafluoro-2-propyl, 2,2,2-trichloroethyl, p-nitrophenylethyl, p-cyanophenylethyl, 9-fluorenylmethyl, 1,3-dithionyl-2-methyl, 2-(trimethylsilyl)ethyl, 2-methylthioethyl, 2-(diphenylphosphino) ethyl, 1-methyl-1-phenylethyl, 3-buten-1-yl, 4-(trimethylsilyl)-2-buten-1-yl, cinnamyl, a-methylcinnamyl, and 8-quinolyl.

3. A compound having the structural formula (I),

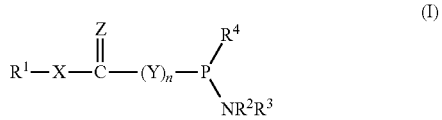

(I)

wherein $R^1$ is hydrogen, $R^2$ and $R^3$ are independently selected from the group consisting of hydrocarbyl, substituted hydrocarbyl, heteroatom-containing hydrocarbyl and substituted heteroatom-containing hydrocarbyl, or $R^2$ and $R^3$ are linked to form a substituted or unsubstituted, five- or six-membered nitrogen-containing heterocycle; $R^4$ is $NR^5R^6$, halogen or DL, wherein $R^5$ and $R^6$ are independently selected from the group consisting of hydrocarbyl, substituted hydrocarbyl, heteroatom-containing hydrocarbyl and substituted heteroatom-containing hydrocarbyl, or $R^5$ and $R^6$ are linked to form a substituted or unsubstituted, five- or six-membered nitrogen-containing heterocycle, D is O, S or NH, and L is a heteroatom-protecting group, unsubstituted hydrocarbyl, substituted hydrocarbyl, heteroatom-containing hydrocarbyl, or substituted heteroatom containing hydrocarbyl; X is O, S, NH, or $NR^7$ wherein $R^7$ is hydrocarbyl, substituted hydrocarbyl, heteroatom-containing hydrocarbyl or substituted heteroatom-containing hydrocarbyl; n is zero or 1; Y is $-(Y')_m-(CR^8R^9)-$ wherein m is zero or 1, Y' is hydrocarbylene, substituted hydrocarbylene, heteroatom-containing hydrocarbylene, or substituted heteroatom-containing hydrocarbylene, wherein $R^8$ and $R^9$ are independently selected from the group consisting of hydrogen, hydrocarbyl, substituted hydrocarbyl, heteroatom-containing hydrocarbyl and substituted heteroatom-containing hydrocarbyl; and Z is O, S, NH or $NR^{10}$ wherein $R^{10}$ is as defined for $R^7$ wherein in any substituted moiety at least one hydrogen atom bound to a carbon atom is replaced by at least one of the following: alkoxy, thio, thioester, halo, amino, nitrile, nitro, sulfonyl, phosphoro, carboxyl, carbonyl, silyl and thienyl.

4. The compound of claim 1, wherein $NR^2R^3$ and $NR^5R^6$ are independently selected from the group consisting of dimethylamino, diethylamino, diisopropylamino, dibutylamino, methylpropylamino, methylhexylamino, methylcyclohexylamino, ethylcyclopropylamino, ethylchloroethylamino, methylbenzylamino, methylphenylamino, thiomorpholino, methyltoluoylamino, methyl-p-chlorophenylamino, methylcyclohexylamino, bromo butylcyclohexylamino, methyl-p-cyanophenylamino, ethyl-cyanoethylamino, piperidino, 2,6-dimethylpiperidino, pyrrolidino, piperazino, isopropylcyclohexylamino, and morpholino.

5. The compound of claim 4, wherein $NR^2R^3$ and $NR^5R^6$ are diisopropylamino.

6. The compound of claim 1, wherein $R^4$ is DL.

7. The compound of claim 6, wherein L is a heteroatom-protecting group removable by an elimination reaction.

8. The compound of claim 7, wherein L is selected from the group consisting of β-cyanoethyl, methyl-β-cyanoethyl, dimethyl-β-cyanoethyl, phenylsulfonylethyl, methyl-sulfonylethyl, p-nitrophenylsulfonylethyl, 2,2,2-trichloro-1,1-dimethylethyl, 2-(4-pyridyl)ethyl, 2-(2-pyridyl)ethyl, allyl, 4-methylene-1-acetylphenol, p-thiobenzoylethyl, 1,1,1,3,3,3-hexafluoro-2-propyl, 2,2,2-trichloroethyl, p-nitrophenylethyl, p-cyanophenylethyl, 9-fluorenylmethyl, 1,3-dithionyl-2-methyl, 2-(trimethylsilyl)ethyl, 2-methylthioethyl, 2-(diphenylphosphino) ethyl, 1-methyl-1-phenylethyl, 3-buten-1-yl, 4-(trimethylsilyl)-2-buten-1-yl, cinnamyl, a-methylcinnamyl and 8-quinolyl.

9. A compound having the structural formula (II)

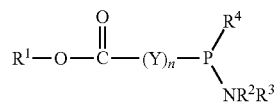

wherein: $R^1$ is hydrogen, lower alkyl, or an electron-withdrawing substituted aliphatic group; $R^2$ and $R^3$ are lower alkyl, or $R^2$ and $R^3$ are linked to form a piperidino, piperazino or morpholino ring; $R^4$ is $NR^5R^6$, chloro or OL wherein $R^5$ and $R^6$ are as defined for $R^2$ and $R^3$, and L is selected from the group consisting of β-cyanoethyl, methyl-β-cyanoethyl, dimethyl-β-cyanoethyl, phenylsulfonylethyl, methyl-sulfonylethyl, p-nitrophenylsulfonylethyl, 2,2,2-trichloro-1,1-dimethylethyl, 2-(4-pyridyl)ethyl, 2-(2-pyridyl)ethyl, allyl, 4-methylene-1-acetylphenol, -thiobenzoylethyl, 1,1,1,3,3,3-hexafluoro-2-propyl, 2,2,2-trichloroethyl, p-nitrophenylethyl, p-cyanophenyl-ethyl, 9-fluorenylmethyl, 1,3-dithionyl-2-methyl, 2-(trimethylsilyl)ethyl, 2-methylthioethyl, 2-(diphenylphosphino)ethyl, 1-methyl-1-phenylethyl, 3-buten-1-yl, 4-(trimethylsilyl)-2-buten-1-yl, cinnamyl, a-methylcinnamyl and 8-quinolyl; n is zero or 1; and Y is $-(Y')_m-(CH_2)-$ wherein m is zero or 1 and Y' is lower alkylene, with the proviso that when n is 1 and m is zero, then $R^1$ is either hydrogen or an electron-withdrawing-substituted aliphatic group.

10. The compound of claim 1, wherein n is zero.
11. The compound of claim 1, wherein n is 1.
12. The compound of claim 11, wherein m is zero.
13. The compound of claim 11, wherein m is 1.
14. The compound of claim 1, wherein Z is O.
15. The compound of claim 14, wherein X is O.
16. A method for phosphitylating a nucleoside or an oligonucleotide having a free 3' or 5' hydroxyl moiety, comprising contacting the nucleoside or oligonucleotide with the compound of claim 1 under conditions effective to convert the free hydroxyl moiety to a phosphino substituent, providing a phosphitylated product.
17. The method of claim 16, wherein the free hydroxyl moiety is a 5' hydroxyl moiety.
18. The method of claim 16, wherein the nucleoside or oligonucleotide is bound to a solid support.
19. The method of claim 16, further comprising reacting the phosphitylated product with an acidic compound effective to convert the phosphitylated product to a nucleoside or oligonucleotide H-phosphonite.
20. In a method for phosphitylating a compound having a nucleophilic moiety using a phosphitylating reagent, the improvement which comprises using as the phosphitylating reagent the compound of claim 1.

* * * * *

SEQUENCE LISTING

```
<160> NUMBER OF SEQ ID NOS: 1

<210> SEQ ID NO 1
<211> LENGTH: 18
<212> TYPE: DNA
<213> ORGANISM: Artificial sequence
<220> FEATURE:
<223> OTHER INFORMATION: chemically synthesized

<400> SEQUENCE: 1
ctcaagtggg ctggtgac                                                   18
```